(12) United States Patent
Fahmy

(10) Patent No.: US 10,500,157 B2
(45) Date of Patent: Dec. 10, 2019

(54) NANOPARTICLE-MEDIATED DELIVERY OF CYTOKINES FOR MAINTENANCE OF THE REGULATORY T CELL PHENOTYPE

(71) Applicant: YALE UNIVERSITY, New Haven, CT (US)

(72) Inventor: Tarek M. Fahmy, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/019,704

(22) Filed: Jun. 27, 2018

(65) Prior Publication Data

US 2018/0369333 A1    Dec. 27, 2018

Related U.S. Application Data

(63) Continuation of application No. 15/155,055, filed on May 15, 2016, now Pat. No. 10,034,917, which is a
(Continued)

(51) Int. Cl.
*A61K 9/127*      (2006.01)
*A61K 47/24*      (2006.01)
(Continued)

(52) U.S. Cl.
CPC ............ *A61K 9/127* (2013.01); *A61K 9/0019* (2013.01); *A61K 9/1271* (2013.01);
(Continued)

(58) Field of Classification Search
CPC .. A61K 9/127; A61K 47/6849; A61K 9/0019; A61K 47/6937; A61K 47/6951;
(Continued)

(56) References Cited

U.S. PATENT DOCUMENTS 5,120,727 A    6/1992    Kao
5,128,355 A    7/1992    Carini
(Continued)

FOREIGN PATENT DOCUMENTS

EP    2177230 A1    4/2010
EP    2389928 A2    11/2011
(Continued)

OTHER PUBLICATIONS

Kazakov and Levon, "Liposome-nanogel structures for future pharmaceutical applications," 2006, Curr Pharm Des 12:4713-28.
(Continued)

*Primary Examiner* — Carlos A Azpuru
(74) *Attorney, Agent, or Firm* — Riverside Law LLP

(57) ABSTRACT

Compositions for delivery of growth factors needed for stable Tregs and methods of use thereof are provided. In preferred embodiments, the compositions can induce, increase, or enhance a functionally robust induced CD4 Treg population (e.g., Foxp3+ Treg) in vivo or ex vivo. The compositions generally include delivery vehicles including TGF-β and IL-2. Delivery vehicles include, for example, polymeric particles, silica particles, liposomes, or multilamellar vesicles. The TGF-β and IL-2 are typically co-loaded into, attached to the surface of, and/or enclosed within the delivery vehicle into the same particle for simultaneous co-delivery to cells such as T cells. Preferably the delivery vehicles are targeted to CD4. The compositions and cells treated therewith can be used in various methods of treating, for example, inflammation, inflammatory and autoimmune diseases and disorders, and inducing or maintaining tolerance including graft and transplant tolerance.

1 Claim, 6 Drawing Sheets

Related U.S. Application Data continuation-in-part of application No. 14/394,161, filed as application No. PCT/US2013/036487 on Apr. 12, 2013, now Pat. No. 9,610,250.

(60) Provisional application No. 61/623,486, filed on Apr. 12, 2012, provisional application No. 61/747,624, filed on Dec. 31, 2012, provisional application No. 61/747,614, filed on Dec. 31, 2012.

(51) Int. Cl.

| | | |
|---|---|---|
| A61K 47/40 | (2006.01) | |
| B82Y 5/00 | (2011.01) | |
| A61K 38/18 | (2006.01) | |
| A61K 38/20 | (2006.01) | |
| A61K 31/343 | (2006.01) | |
| A61K 47/58 | (2017.01) | |
| A61K 47/69 | (2017.01) | |
| A61K 47/68 | (2017.01) | |
| A61K 9/00 | (2006.01) | |
| A61K 9/51 | (2006.01) | |
| C07K 16/28 | (2006.01) | |

(52) U.S. Cl.
CPC .......... *A61K 9/1273* (2013.01); *A61K 9/1277* (2013.01); *A61K 9/5153* (2013.01); *A61K 31/343* (2013.01); *A61K 38/1841* (2013.01); *A61K 38/2013* (2013.01); *A61K 47/24* (2013.01); *A61K 47/40* (2013.01); *A61K 47/58* (2017.08); *A61K 47/6849* (2017.08); *A61K 47/6937* (2017.08); *A61K 47/6951* (2017.08); *B82Y 5/00* (2013.01); *C07K 16/2812* (2013.01)

(58) Field of Classification Search
CPC .... A61K 47/58; A61K 9/1277; A61K 31/343; A61K 38/1841; A61K 38/2013; A61K 9/1273; A61K 9/1271; A61K 47/40; A61K 47/24; C07K 16/2812; B82Y 5/00
See application file for complete search history.

(56) References Cited

U.S. PATENT DOCUMENTS

| | | | |
|---|---|---|---|
| 5,138,069 | A | 8/1992 | Carini |
| 5,153,197 | A | 10/1992 | Carini |
| 5,155,118 | A | 10/1992 | Carini |
| 5,162,333 | A | 11/1992 | Failli |
| 5,202,332 | A | 4/1993 | Hughes |
| 5,210,079 | A | 5/1993 | Carini |
| 5,354,867 | A | 10/1994 | Carini |
| 5,385,908 | A | 1/1995 | Nelson |
| 5,484,790 | A | 1/1996 | Failli |
| 5,530,006 | A | 6/1996 | Waranis |
| 5,559,112 | A | 9/1996 | Skotnicki |
| 5,567,709 | A | 10/1996 | Skotnicki |
| 5,780,462 | A | 7/1998 | Lee |
| 5,989,591 | A | 11/1999 | Nagi |
| 6,015,809 | A | 1/2000 | Zhu |
| 7,052,694 | B2 | 5/2006 | Pease |
| 7,390,888 | B2 | 6/2008 | Pease |
| 7,411,051 | B2 | 8/2008 | Rosen |
| 8,114,845 | B2 | 2/2012 | Langermann |
| 8,263,125 | B2 | 9/2012 | Vaya |
| 8,609,089 | B2 | 12/2013 | Langermann |
| 8,709,416 | B2 | 4/2014 | Langermann |
| 9,603,800 | B2 | 3/2017 | Fahmy |
| 2003/0035842 | A1 | 2/2003 | Kazakov |
| 2004/0071761 | A1 | 4/2004 | Miller |
| 2006/0099203 | A1 | 5/2006 | Pease |
| 2006/0110383 | A1 | 5/2006 | Honjo |
| 2007/0014845 | A1* | 1/2007 | Zhang .................. A61K 9/0019 424/450 |
| 2007/0166281 | A1 | 7/2007 | Kosak |
| 2007/0168281 | A1 | 7/2007 | Kosak |
| 2007/0219122 | A1 | 9/2007 | Glazer |
| 2008/0050920 | A1 | 2/2008 | Kawahara |
| 2008/0187595 | A1 | 8/2008 | Jordan |
| 2009/0004213 | A1 | 1/2009 | Singh |
| 2011/0262406 | A1 | 10/2011 | Del |
| 2015/0064265 | A1 | 3/2015 | Fahmy |
| 2015/0118318 | A1 | 4/2015 | Fahmy |

FOREIGN PATENT DOCUMENTS

| | | |
|---|---|---|
| EP | 2494960 A1 | 9/2012 |
| WO | 9504738 A1 | 2/1995 |
| WO | 9515746 A1 | 6/1995 |
| WO | 9516691 A1 | 6/1995 |
| WO | 9522972 A1 | 8/1995 |
| WO | 0001385 A1 | 1/2000 |
| WO | 03099196 A2 | 12/2003 |
| WO | 2004004771 A1 | 1/2004 |
| WO | 2004056875 A1 | 7/2004 |
| WO | 2006121168 A1 | 11/2006 |
| WO | 2006133396 A2 | 12/2006 |
| WO | 2007005754 A2 | 1/2007 |
| WO | 2007005874 A2 | 1/2007 |
| WO | 2007056539 A2 | 5/2007 |
| WO | 2007072286 A2 | 6/2007 |
| WO | 2008083174 A2 | 7/2008 |
| WO | 2009014708 A2 | 1/2009 |
| WO | 2009073533 A2 | 6/2009 |
| WO | 2010083337 A2 | 7/2010 |
| WO | 2012009611 A2 | 1/2012 |
| WO | 2012068531 A2 | 5/2012 |
| WO | 2015066535 A1 | 5/2015 |

OTHER PUBLICATIONS

Van Thienen, "Protein Release from Biodegradable Dextran Nanogels," 2007, Langmuir 23:9794-801.
Moya-Ortega et al., "Cyclodextrin-based nanogels for pharmaceutical and biomedical applications," 2012, Int J Pharm 428:152-63.
Regen, "Polymerized phosphatidylcholine vesicles as drug carriers," 1985, Ann N Y Acad Sci 446 296-07.
Lee et al., "Amphiphilic poly(D,L-lactic acid)/poly(ethylene glycol)/poly(D,L-lactic acid) nanogels for controlled release of hydrophobic drugs," 2006, 6(10):846-54.
Chen, et al. 'Evaluation of ion-exchange microspheres as carriers for the anticancer drug doxorubicin: in vitro studies.' J. Pharm. Pharmacol. 44(3):211-5 (1992).
Farag, et al. 'Rate of release of organic carboxylic acids from ion exchange resins' J. Pharm. Sci. 77(10):872-5(1988).
Gorelik, et al., 'Immune-mediated eradication of tumors through the blockade of transforming growth factor-beta signaling in T cells', Nat Med., 7(10):1118-22 (2001).
Hu, et al., "Reaction parameters of targeted gene repair in mammalian cells", Mol. Biotech., 29:197-210 (2005).
Olsen, et al., 'Genomic sequence correction by single-stranded DNA oligonucleotides: role of DNA synthesis and chemical modifications of the oligonucleotide ends'. J. Gene Med., 7:1534-44 (2005).
Peer, et al., "Systemic leukocyte-directed siRNA delivery revealing cyclin D1 as an anti-inflammatory target", Science, 319:627-30 (2008).
Petersen, et al., 'Accumulation in tumor tissue of adoptively transferred T cells: A comparison between intravenous and intraperitoneal injection', J Immunother 29, 241-9 (2006).
Ruoslahti, et al., 'Specialization of tumour vasculature', Nat. Rev. Cancer, 2:83-90 (2002).
Samstein, et al., 'The use of deoxycholic acid to enhance the oral bioavailability of biodegradable nanoparticles', Biomaterials., 29(6):703-8 (2008).
Sawhney, et al., 'Bioerodible hydrogels based on photopolymerized poly(ethylene glycol)-co-poly(.alpha.-hydroxy acid) diacrylate macromers', Macromolecules, 26:581-7 (1993).

(56) References Cited

OTHER PUBLICATIONS

Altincicek, et al., 'Identification of collagen IV derived danger/alarm signals in insect immunity by nanoLC-FTICR MS', 2009, Biol Chem., 390:1303-11.
Anderson and Shive, et al., "Biodegradation and biocompatibility of PLA and PLGA microspheres," 1997, Adv Drug Deliv Rev 28(1):5-24.
Argyo, et al., "Multifunctional Mesoporous Silica Nanoparticles as a Universal Platform for Drug Delivery", 2014, Chem. Mater., 26(1):435-451.
Aubert, et al., "Antigen-specific CD4 T-cell help rescues exhausted CD8 T cells during chronic viral infection," 2011, PNAS, 108:21182-7.
Barbe, et al., "Silica Particles: A Novel Drug-Delivery System," 2004, Advanced Materials, 16(21):1959-66.
Berger et al., "Phase I safety and pharmacokinetic study of CT-011, a humanized antibody interacting with PD-1, in patients with advanced hematologic malignancies," 2008, Clin. Cancer Res., 14:3044-51.
Blanco, et al., "Induction of dendritic cell differentiation by IFN-alpha in systemic lupus erythematosus," 2001, Science 294(5546)1540-3.
Blanco, et al., "Nanomedicine in cancer therapy: innovative trends and prospects," 2011, Cancer Sci, 102(7):1247-52.
Bonifaz, et al., 'Efficient targeting of protein antigen to the dendritic cell receptor DEC-205 in the steady state leads to antigen presentation on major histocompatibility complex class I products and peripheral CD8+ T cell tolerance', J. Exp. Med., 196(12)1627-38 (2002).
Bonifaz, et al., "In vivo targeting of antigens to maturing dendritic cells via the DEC-205 receptor improves T cell vaccination," 2004, J. Exp. Med., 199(6):815-24.
Braumuller, et al., "T-helper-1-cell cytokines drive cancer into senescence," 2012, Nature, 494:361-365.
Butte, et al., "Programmed death-1 ligand 1 interacts specifically with the B7-1 costimulatory molecule to inhibit T cell responses", Immunity, vol. 27, pp. 111-122, (2007).
Capurso, et al., 'Development of a nanoparticulate formulation of retinoic acid that suppresses Th17 cells and upregulates regulatory T cells', Self Nonself, 1:4:335-40 (2010).
Chen, et al., 'A facile construction strategy of stable lipid nanoparticles for drug delivery using a hydrogel-thickened microemulsion system', 2010, Nanotechnoiogy 21:015101.
Clarke, et al., 'Cancer stem cells—perspectives on current status and future directions: AACR Workshop on cancer stem cells', Cancer Res., 66:9339-9344 (2006).
Corradetti, et al., "Paracrine signaling events in embryonic stem cell renewal mediated by affinity targeted nanoparticles", Biomaterials, 33(28):6634-43 (2012).
Corthay, et al., "Primary antitumor immune response mediated by CD4+ T cells", Immunity, 22, 371-83 (2005).
Cubillos-Ruiz, et al., "Polyethylenimine-based siRNA nanocomplexes reprogram tumor-associated dendritic cells via TLR5 to elicit therapeutic antitumor immunity", J. Clin. Invest. 119(8): 2231-44 (2009).
Curiel, 'Regulatory T cells and treatment of cancer', Curr. Opin. Immunol., 20(2):241-6 (2008).
DaCosta, et al., 'SB-505124 is a selective inhibitor of transforming growth factor-beta type I receptors ALK4, ALK5, and ALK7', Mol Pharmacol. 65:744-52 (2004).
Dalerba, et al., 'Cancer stem cells: models and concepts', Annu. Rev. Med., 58:267-84 (2007).
Danhier, et al., 'PLGA-based nanoparticles: an overview of biomedical applications', J. Control Release, 161(2):505-22 (2012).
De Rezende, et al., 'Regulatory T cell as a target for cancer therapy', Arch. Immunol. Ther. Exp., 58(3):179-90 (2010).
Demento, et al., 'Inflammasome-activating nanoparticles as modular systems for optimizing vaccine efficacy', Vaccine, 27(23):3013-21 (2009).
Demento, et al., "Role of sustained antigen release from nanoparticle vaccines in shaping the T cell memory phenotype", Biomaterials, 33(19):4957-64 (2012).
Egilmez et al., "Cytokine immunotherapy of cancer with controlled release biodegradable microspheres in a human tumor xenograft/SCID mouse model," 1998, Cancer Immunol. Immunother. 46:21-24.
Elamanchili, et al., 'Characterization of poly(D,L-lactic-co-glycolic acid) based nanoparticulate system for enhanced delivery of antigens to dendritic cells', Vaccine, 22(19):2406-12 (2004).
Elbarbry, et al., 'Liquid chromatographic determination of mycophenolic acid and its metabolites in human kidney transplant plasma: pharmacokinetic application', J Chromatogr B Analyt Technol Biomed Life Sci, 859(2):276-81(2007).
Erbe, et al., 'Small molecule ligands define a binding site on the immune regulatory protein B7.1.', J. Biol. Chem., 277:7363-8 (2002).
Fahmy, et al., 'Targeted for drug delivery', Materials Today, 8(8):18-26 (2005).
Filler, et al., 'Random pharmacokinetic profiles of EC-MPS in children with autoimmune disease', Pediatric Rheumatol., 8:1 (2010).
Freeman, "Structures of PD-1 with its ligands: sideways and dancing cheek to cheek", PNAS, 105:10275-6 (2008).
Frey, et al., 'Signaling defects in anti-tumor T cells', Immunol. Rev., 222:192-205 (2008).
Ginzler, et al., 'Mycophenolate mofetil or intravenous cyclophosphamide for lupus nephritis', N Engl J Med, 353(21):2219-28 (2005).
Grell, et al., 'The transmembrane form of tumor necrosis factor is the prime activating ligand of the 80 kDa tumor necrosis factor receptor', Cell, 83:793-802 (1995).
Guo, et al., 'Losartan downregulates the expression of transforming growth factor beta type I and type II receptors in kidney of diabetic rat.', Zhonghua Nei Ke Za Zhi, 42:403-8 (2003).
Hamidi, et al., 'Hydrogel nanoparticles in drug delivery', Adv Drug Deily Rev., 60(15):1638-49 (2008).
Hawiger, et al., "Dendritic cells induce peripheral T cell unresponsiveness under steady state conditions in vivo", J. Exp. Med., 194(6):769-79 (2001).
Health Day, 'Blood pressure drug might boost chemo success, mouse study suggests', http://consumer.healthday.com/circulatory-system-information-7/blood-pres- sure-news-70/blood-pressure-drug-might-boost-chemo-success-mouse-study-sug- gests-680633.html,Retrieved from the internet Oct. 2, 2013. (1 page).
Honeychurch, et al., 'Anti-CD40 monoclonal antibody therapy in combination with irradiation results in a CD8 T-cell-dependent immunity to B-cell lymphoma', Blood, 102:1449-1457 (2003).
Hunder, et al., 'Treatment of metastatic melanoma with autologous CD4+ T cells against NY-ESO-1', NEJM, 358:2698-2703 (2008).
Jain, et al., "Nanolipobeads bases drug delivery system for effective management of peptic ulcer", Intl J Curr Pharmaceutical Res., 3(2):141-9 (2011).
Jonsson, et al., 'Inosine monophosphate dehydrogenase (IMPDH) inhibition in vitro suppresses lymphocyte proliferation and the production of immunoglobulins, autoantibodies and cytokines in splenocytes from MRLlpr/lpr mice', Clin Exp Immunol, 124(3):486-91 (2001).
Jonsson, et al., "Mycophenolic acid inhibits inosine 5'-monophosphate dehydrogenase and suppresses immunoglobulin and cytokine production of B cells", Int Immunopharmacol, 3(1):31-7 (2003).
Joshi, et al., 'Targeting tumor antigens to dendritic cells using particulate carriers', J. Control Release, 161(1):25-37 (2012).
Kahn, 'CD4+ T cell clones specific for the human p97 melanoma-associated antigen can eradicate pulmonary metastases from a murine tumor expressing the p97 antigen', J Immunol, 146:3235-41 (1991).
Karnell, et al., "Mycophenolic acid differentially impacts B cell function depending on the stage of differentiation", J Immunol, 187(7):3603-12 (2011).
Kong, et al., 'Combination therapy with losartan and piog;otazone additively reduces renal oxidative and nitrative stress induced by chronic high fat, sucrose, and sodium intake', Oxid Med Cell. Longev, doi: 10.1155/2012/856085 (2012). (10 pages).

(56) References Cited

OTHER PUBLICATIONS

Lagaraine, et al., 'Induction of human CD4+ regulatory T cells by mycophenolic acid-treated dendritic cells', J Leukoc Biol, 84(4):1057-64 (2008).
Lagaraine, et al., 'Mycophenolic acid-treated human dendritic cells have a mature migratory phenotype and inhibit allogeneic responses via direct and indirect pathways', Int Immunol, 17(4):351-63 (2005).
Lazar-Molnar, et al., 'Crystal structure of the complex between programmed death-1 (PD-1) and its ligand PD-L2', PNAS, 105:10483-8 (2008).
Lee, et al., "Induction and maintenance therapy for lupus nephritis: a systematic review and meta-analysis", Lupus, 19(6):703-10 (2010).
Lipsky, 'Mycophenolate mofetil', Lancet, 348:L1357-9 (1996).
Look, et al., 'Application of nanotechnologies for improved immune response against infectious diseases in the developing world', Adv Drug Deilv Rev, 62(4-5):378-93 (2010).
Look, et al., 'Nanogel-based delivery of mycophenolic acid ameliorates systemic lupus erythematosus in mice', J. Clin Invest., 123(4):1741-9 (2013).
Look, et al., 'The nanomaterial-dependent modulation of dendritic cells and its potential influence on therapeutic immunosuppression in lupus', Biomaterials, 35(3):1089-95 (2014).
Losartan, from Wikipedia encyclopedia, https://en.wikipedia.org/wiki/Losartan, 4 pages, retrieved from the internet Oct. 22, 2013.
Luchini, et al. 'Smart hydrogel nanoparticles for serum cancer biomarkers harvesting', AACR annual meeting, Apr. 14-18, Los Angles Ca, 2007. (1 page).
Lui, et al., 'Effect of mycophenolate mofetil on severity of nephritis and nitric oxide production in lupus-prone MRL/lpr mice', Lupus, 11(7):411-8 (2002).
Lund, et al., 'Toll-like receptor 9-mediated recognition of Herpes simplex virus-2 by plasmacytoid dendritic cells', J Exp Med, 198(3):513-20 (2003).
Matreya, '1,2-Distearoylphosphatidylethanolamine-methyl-polyethyleneglycol conjugate-200(Na+salt)', http://www.matreya.com/ProductInfo.aspx?peoductid=1439, 2 pages, retrieved from the Internet Mar. 30, 2012. (2 pages).
Maurer, et al., 'Developments in liposomal drug delivery systems', Expert Opin Biol Ther., 1(6):923-47 (2001).
Mehling, et al., Mycophenolate mofetil impairs the maturation and function of murine dendritic cells, J Immunol, 165(5):2374-81 (2000).
Monneaux, et al., 'Molecular therapies for systemic lupus erythematosus: clinical trials and future prospects', Arthritis Res Ther, 11(3):234 (2009).
Moroni, et al., 'A randomized pilot trial comparing cyclosporine and azathioprine for maintenance therapy in diffuse lupus nephritis over four years', Olin J Am Soc Nephrol, 1(5):925-32 (2006).
Mougiakakos, et al., 'Regulatory T cells in cancer', Adv Cancer Res, 107:57-117 (2010).
Nagaraj, et al., 'Anti-inflammatory triterpenoid blocks immune suppressive function of MDSCs and improves immune response in cancer', Clin Cancer Res., 16(6):1812-23 (2010).
Navarra, et al., 'Efficacy and safety of belimumab in patients with active systemic lupus erythematosus: a randomised, placebo-controlled, phase 3 trial', Lancet, 377(9767):721-31 (2011).
Nesbeth, et al., 'CD4+ T cells elicit host immune responses to MHC class II-negative ovarian cancer through CCL5 secretion and CD40-mediated licensing of dendritic cells', J Immunol., 184:5654-62 (2010).
Oda, et al., 'Transforming growth factor .sup.2 (TGF-.sup.2) and regulatory T cells (Treg): The interface of tumor and host immunity,' European journal of clinical & medical oncology 4(1):27-32 (2011).
Opal and DePalo, 'Anti-inflammatory cytokines', Chest, 117(4):1162-72 (2000).
Park, 'Rationally engineered nanoparticles for therapeutic modulation of transforming growth factor beta signaling', Dissertation confidentially presented May 2011, not publically available other than abstract from ProQuest UMI No. 3467563, pp. 1-25 only distributed to one party prior to filing of U.S. Appl. No. 61/623,486, filed Apr. 12, 2012.
Patel, et al., 'Review on hydrogel nanoparticles in drug delivery' AJPTR, 1(3):19-38 (2011).
Perez-Diez, 'CD4 cells can be more efficient at tumor rejection than CD8 cells' Blood, 109:5346-54 (2007).
Punyamoonwongsa and Tighe, 'A smart hydrogel-based system for controlled drug release', Chiang Mai J Sci., 32(3):471-8 (2005).
Quemeneur, et al., Mycophenolic acid inhibits IL-2-dependent T cell proliferation, but not IL-2-dependent survival and sensitization to apoptosis, J Immunol, 169(5):2747-55 (2002).
Rahman, et al., 'Systemic lupus erythematosus', N Engl J Med, 358(9):929-39 (2008).
Ramos, et al., 'Modulation of autoantibody production by mycophenolate mofetil: effects on the development of SLE in (NZB x NZW)F1 mice', Nephrol Dial Transplant, 18(5):878-83 (2003).
Rehman, et al., "Angiotensin Type 2 receptor agonist compound 21 reduces vascular injury and myocardial fibrosis in stroke-prone spontaneously hypertensive rats", Hypertension, 59(2):291-9 (2012).
Ronnblom, et al., 'Cytokines as therapeutic targets in SLE', Nat Rev Rheumatol, 6(6):339-47 (2010).
Ruoslahti, et al., "RGD and other recognition sequences for integrins", Annu. Rev. Cell Dev. Biol., 12:697-715 (1996).
Sammartino, et al., 'Anti-GBM disease following CTLA4 blockade in a patient with metastatic melanoma', Clinical Kidney J, 3(2):135-137 (2010).
Schneider, et al., 'Conversion of membrane-bound Fas(CD95) ligand to its soluble form is associated with downregulation of its proapoptotic activity and loss of liver toxicity', J. Exp. Med.,187:1205-121 (1998).
Scindia, et al., 'Anti-alpha8 integrin immunoliposomes in glomeruli of lupus-susceptible mice: a novel system for delivery of therapeutic agents to the renal glomerulus in systemic lupus erythematosus', Arthritis Rheum, 58(12):3884-91 (2008).
Selleckchem,'TGF-beta/Smad Inhibitors' http://www.selleckchem.com/products/sb-505124.html, 4 pages, Retrieved from the internet Oct. 22, 2013.
Serkova, et al., 'Renal inflammation: targeted iron oxide nanoparticles for molecular MR imaging in mice', Radiology, 255(2):517-26 (2010).
Sfikakis, et al., 'Rituximab anti-B-cell therapy in systemic lupus erythematosus: pointing to the future', Curr Opin Rheumatol, 17(5):550-7 (2005).
Shafer-Weaver, et al., 'Immunity to murine prostatic tumors: continuous provision of T-cell help prevents CD8 T-cell tolerance and activates tumor-infiltrating dendritic cells', Cancer Research, 69:6256-64 (2009).
Shirali, et al., 'Nanoparticle delivery of mycophenolic acid upregulates PD-L1 on dendritic cells to prolong murine allograft survival', Am J Transplant, 11(12):2582-92 (2011).
Shlomchik, et al., 'From T to B and back again: positive feedback in systemic autoimmune disease', Nat Rev Immunol, 1(2):147-53 (2001).
Tanaka, et al., "Downregulation of Fas ligand by shedding", Nat. Med., 4: 31-36 (1998).
Teichmann, et al., 'Dendritic cells in lupus are not required for activation of T and B cells but promote their expansion, resulting in tissue damage', Immunity, 33(6):967-78 (2010).
Torchilin, et al., 'Multifunctional nanocarriers', Adv Drug Deliv Rev., 58(14):1532-55 (2006).
Trevelyan, et al., 'Effect of enalapril and losartan on cytokines in patients with stable angina pectoris awaiting coronary artery bypass grafting and their interaction with polymorphisms in the interleukin-6 gene', Am J Caridol., 94(5):564-9 (2004).
Triantafyllopoulou, et al., 'Proliferative lesions and metalloproteinase activity in murine lupus nephritis mediated by type I interferons and macrophages', PNAS, 107(7):3012-7 (2010).
Vonderheide, "Prospect of targeting the CD40 pathway for cancer therapy", Clin Cancer Res, 13(4):1083-1088 (2007).
Wadia, et al., "Mycophenolic acid inhibits maturation and function of human dendritic cells and B cells", Hum Immunol, 70(9):692-700 (2009).

(56) References Cited

OTHER PUBLICATIONS

Wang, et al., 'Immune suppression by tumor-specific CD4+ regulatory T-cells in cancer', Semin Cancer Biol., 16:73-9 (2006).
Willimsky, et al., 'The adaptive immune response to sporadic cancer', Immunol. Rev., 220:102-12 (2007).
Wofsy, et al., 'Reversal of advanced murine lupus in NZB/NZW F1 mice by treatment with monoclonal antibody to L3T4', J Immunol, 138(10):3247-53 (1987).
Wofsy, et al., 'Successful treatment of autoimmunity in NZB/NZW F1 mice with monoclonal antibody to L3T4', J Exp Med, 161(2):378-91 (1985).
Yang, et al., 'Preparation of gel-core-solid lipid nanoparticle: A novel way to improve the encapsulation of protein and peptide', Chem Pharm Bull., 58(9):1195-202 (2010).
Yoshida, et al., 'Effect of poly(lactic-co-glycolic acid) contact on maturation of murine bone marrow-derived dendritic cells', J Biomed Mater Res A, 80(1):7-12 (2007).
Ziai, et al., 'Renal allograft protection with losartan in Fisher Lewis rats: Hemodynamics, macrophages, and cytokines', Kidney Int., 57(6):2618-25 (2000).
Cavalli, et al., 'Solid lipid nanoparticies as carriers of hydrocortisone and progesterone complexes with beta-cyclodextrins', Intl J Pharma., 182:59-69 (1999).
Clawson, et al., 'Synthesis and characterization of lipid-polymer hybrid nanoparticles with pH-triggered PeG shedding', Langmuir, 27(17):10556-61 (2011).
De Miguel, et al., "Proofs of the structure of lipid coated nanoparticles (SMBV) used as drug carriers", Pharma Res., 17(7):817-24 (2000).
Diop-Frimpong, et al., 'Losartan inhibits collagen I synthesis and improves the distribution and efficacy of nanotherapeutics in tumors', PNAS, 108(7):2909-14 (2011).
Flavell, et al., The polarization of immune cells in the tumour enviroment by TGFbeta, Nat Rev Immunol., 10(8):1-27 (2010).
Hoare, et al., 'Hydrogels in drug delivery: Process and challenges', Polymer, 49:1993-2007 (2008).
Hong, 'Lipid-hydrogel nanoparticles synthesis methods and characterization',Theses from DRUM, pp. 1-91 (2009).
Jhunjhunwala, et al., 'Controlled release formulations of IL-2, TGF-21 and rapamycin for the induction of regulatory T cells', J Cont Rel., 159(1):78-84 (2012).
Khalil, et al., "Angiotensin II type 1 receptor antagonist (losarian) down-regulates transforming growth factor-beta in experimental acute pyelonephritis," 2000, J Urology, 164(1):186-91.
Ma et al., 'The comparison of different daidzein-PLGA nanoparticles in increasing its oral bioavailability', Int J Nanomed., 7:559-570 (2012).
Mura, et al., "Development of a new delivery system consisting in drug-in cyclodextrin-in PLGA nanoparticles", J Microencapsulation, 27(6):479-86 (2010).
Murphy, et al., "Targeted Nanogels: A Versatile Platform for Drug Delivery to Tumors", Mole Cancer Therapeutics, 10(6):972-82 (2011).
Park, et al., "Combination delivery TGF-2 inhibitor and IL-2 nanoscale liposomal polymeric gels enhances tumor immunotherapy," 2012, Nat Mater., 11(20):895-905.
Steenblock, et al., 'A Comprehensive Platform for Ex Vivo T-cell Expansion Based on Biodegradable Polymeric Artificial Antigen-presenting Cells', Mole Therapy, 16(4):765-72 (2008).
Wong, et al., 'Simultaneous delivery of doxorubicin and GG918 (Elacridar) by new polymer-lipid hybrid nanoparticles (PLN) for enhanced treatment of multidrug-resistant breast cancer', J Cont Rel., 116:275-84 (2006).
Xiao, et al., 'Recent advances in PEG-PLA block copolymer nanoparticles', Int J Nanomed., 5:1057-65 (2010).
Zhang, et al., 'Self-assembled lipid-polymer hubrid nanoiparticles: A robust drug delivery platform', ACS Nano, 2(8):1696-1702 (2008).

\* cited by examiner

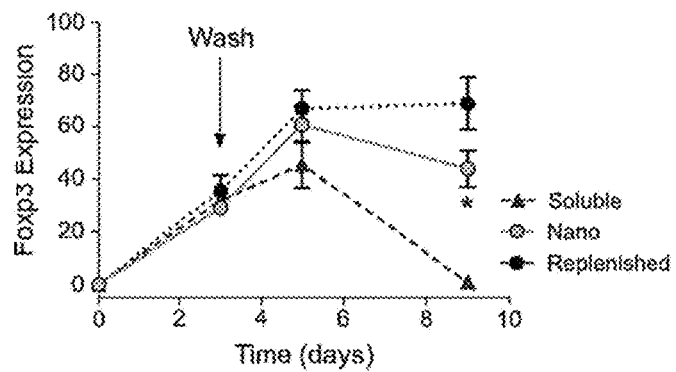
FIG. 5
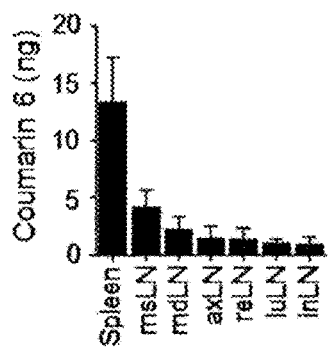
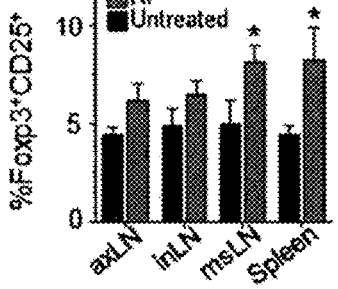
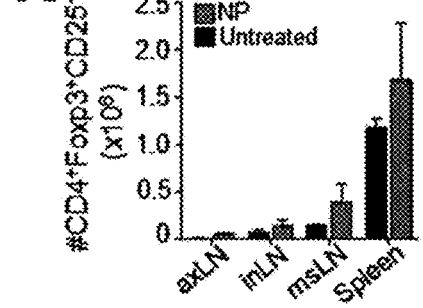
FIG. 6A-6C

NANOPARTICLE-MEDIATED DELIVERY OF CYTOKINES FOR MAINTENANCE OF THE REGULATORY T CELL PHENOTYPE

CROSS REFERENCE TO RELATED APPLICATIONS

The present application is a continuation of U.S. patent application Ser. No. 15/155,055, filed on May 15, 2016, which is a continuation-in-part of U.S. patent application Ser. No. 14/394,161, filed Oct. 13, 2014, which is a U.S. national phase application filed under 35 U.S.C. § 371 claiming benefit to International Patent Application No. PCT/US2013/036487, filed Apr. 12, 2013, which is entitled to priority to U.S. Provisional Application No. 61/623,486, filed Apr. 12, 2012, U.S. Provisional Application No. 61/747,624, filed Dec. 31, 2012, and U.S. Provisional Application No. 61/747,614, filed Dec. 31, 2012, each of which applications is incorporated herein by reference in their entireties.

STATEMENT REGARDING FEDERALLY SPONSORED RESEARCH OR DEVELOPMENT

This invention was made with government support under AI056363 awarded by National Institute of Health. The government has certain rights in the invention.

FIELD OF THE INVENTION

The present invention is generally in the field of delivery of the combination of IL-2 and TGF-β, using nanoparticulates, which may be targeted to CD4 expressed by a desired cell or tissue type to enhance efficacy

BACKGROUND OF THE INVENTION

CD4+ T cells represent an intriguing checkpoint for therapeutic intervention in immune-mediated diseases. This is because the differentiation and subsequent function of CD4+ T cells can be controlled through: 1) manipulation of the T cell receptor (TCR) signaling, 2) modulation of co-stimulatory or inhibitory molecules, and 3) influencing the cytokine milie u. In this context, the cytokine milieu is important for the orchestration of lineage development steps towards either effector T cell (Teff) or regulatory T cell (Treg) phenotypes. As such, the role of cytokines in the differentiation of CD4+ T cells serves as an excellent example to describe the common difficulties encountered in the therapeutic manipulation of immune cell function in physiopathological conditions. One major challenge is the requirement for targeted and highly localized delivery of cytokines to CD4+ cells and not to other cells, because of the pleiotropic effects of cytokines on certain immune cell populations. Another attribute of cytokines is redundancy, and one more intriguing aspect of the immune response is that the combination of certain cytokines can exert well-defined effects only on selected immune cell populations. For example, the combination of TGF-β and IL-2 during antigenic stimulation results in the differentiation of naïve CD4+ T cells into Tregs. However, the simultaneous signaling by TGF-β and the inflammatory cytokine IL-6 not only suppresses the formation of tolerogenic Tregs, but also induces the development of proinflammatory Th17 cells, which have a key promoting role in the pathogenesis of autoimmune disease such as SLE.

Although Tregs have an unequivocal protective role in autoimmune disease, the possible therapeutic use of cytokines for the induction of Tregs is complicated by the fact that an indiscriminate use in vivo of either TGF-β or IL-2 would not be a viable option. In particular, TGF-β is pro-fibrotic, while IL-2 acts on all T cells (thus expanding concurrently both Tregs and Teff populations). Another technical challenge is that a generalized delivery of TGF-β and IL-2 in vivo could result in synergy or counter-regulation of Tregs outcome if other cytokines are present concomitantly in the local milieu.

Tregs that express the Forkhead box protein transcription factor (Foxp3) are a critical subset of CD4+ T cells that maintain homeostasis during infection and tolerance toward self-epitopes. Mutations in Foxp3 can lead to the wasting multiorgan autoimmune condition, IPEX (immune-dysregulation, poly-endocrinopathy, enteropathy, X-linked) in humans. In many common autoimmune diseases such as multiple sclerosis and type 1 diabetes, Tregs become unable to control pathogenic CD4 and CD8 effector cells because of defects on numbers or function. For this reason, strategies to correct these defects and boost their stability have been garnering attention as potential alternatives to the conventional broadly immunosuppressive agents currently in use.

Foxp3+ Tregs are now classified as one of three subsets. The majority of endogenous Tregs, now called nTregs, originate in the thymus and are called tTregs. Others called pTregs are induced from naïve T cells in the periphery. nTregs characteristically display chromatin demethylation at the Foxp3 locus. Tregs require the cytokines IL-2 and TGF-β for fitness and survival. Tregs similar to pTregs called iTregs can also be induced from naïve CD4+ cells ex-vivo by suboptimal TCR signaling in the presence of IL-2 and TGF-β. iTregs were initially believed to be unstable because chromatin remained methylated at the Foxp3 locus. However, in an inflammatory microenvironment nTregs are also unstable and can convert to an effector phenotype. Importantly, recent studies comparing the stability of mouse and human nTregs and iTregs in an inflammatory microenvironment have revealed that only iTregs remain Foxp3+ and can reverse established disease. These findings are supported by the report that Tregs induced in-vivo can also reverse disease in animal models of multiple sclerosis and autoimmune diabetes. However, the methods used to induce these protective iTregs are probably too toxic for translation into a practical immunotherapy.

Thus it is an objection of the invention to provide compositions and methods of use thereof able to safely provide the growth factors needed for stable Tregs.

It is a further object of the invention to provide compositions and methods of use thereof to generate a functionally robust induce CD4 Treg population in-vivo.

SUMMARY OF THE INVENTION

Compositions and methods for directed delivery of active agents to immune cells are provided. The compositions generally include a delivery vehicle such as polymeric particles, silica particles, liposomes, or multilamellar vesicles with TGF-β and IL-2 co-loaded into, attached to the surface of, and/or enclosed within. Preferably the delivery vehicle is a polymeric particle, for example a PLGA nanoparticle. The delivery vehicles are optionally, but preferably, targeted to CD4 by a targeting moiety such as anti-CD4 antibody.

Experiments demonstrate the importance of antigen persistence mediated by particulate platforms and its role in the long-term appearance of effector memory cellular response. Systemic administration of CD4-targeted cytokine-loaded nanoparticles ("NPs") was able to promote tolerance through expansion of host regulatory cells in murine allograft models. CD4-targeted TGF-β/IL-2 NPs alone induced a 3% increase in Treg frequency in the spleen and mesenteric lymph nodes of healthy mice. Donor-specific transfusion of splenocytes pretreated with CD4-targeted LIE nanoparticles NPs resulted in a 4-fold increase in donor-specific Tregs and significantly enhanced tolerance of fully mismatched heart allografts from 7 to 12 days.

Targeted nanoparticles (NPs) offer an innovative solution to the challenges outlined above. Compared to soluble cytokines, NPs have the advantage to: 1) shift the biodistribution of cytokines selectively to target cells, thereby localizing cytokine effects to cells of interest; 2) deliver relatively high local doses (if needed), while diminishing the need for large systemic doses and related side effects; 3) exploit existing synergies or counter-regulatory mechanisms through the simultaneous delivery of multiple components under a single platform.

Under these considerations, the use of NPs to augment the proven beneficial effects of adoptive T cell transfer or direct immunotherapy can represent a significant innovation that offers advantages over existing best practices, since it optimizes the induction of protective mechanisms of action at the target site while minimizing concomitant side effects. Additional benefits in the use of NPs are: 4) the capacity to deliver bioactive molecules specifically to target cells over sustained periods of time; 5) a delivery under dynamic physiologic conditions (such as those occurring after adoptive transfer), with the advantage of a fine tuning for optimization of the response.

Thus compositions including particles, including polymer nanoparticles, loaded with a combination of TGF-β and IL-2, optionally, but preferably targeted to CD4 are provided. The composition can be in an amount effective amount to increase Treg frequency, number, or a combination thereof in a subject. The compositions can be administered to subjects in need thereof to increase Treg frequency, number, or a combination thereof in the subject. The composition can be administered systemically. Methods of increasing donor-specific Tregs are also provided. Exemplary methods include treating isolated cells, for example leukocytes, ex vivo with particles co-loaded with TGF-β and IL-2. The cells can be administered to a subject in need thereof to induce or increase tolerance, for example graft tolerance, in the subject.

BRIEF DESCRIPTION OF THE DRAWINGS

FIG. 5 is a line graph showing Foxp3 expression monitored over time on mixed splenocytes treated with soluble (triangles) or nano-encapsulated (circles) TGF-β and IL-2 for a 3 day induction phased before washing the cells and replating. Control cells (circles) were replenished with soluble cytokine after washing. (*p<0.05 between nano-encapsulated and soluble using a 2-tailed T test on day 9 Foxp3 expression).

FIG. 6A is a bar graphs showing coumarin-6 (ng) in tissues harvested five days after I.P. injection of 2.0 mg coumarin-6 labeled nanoparticles. Coumarin-6 was measured by fluorescence microscopy. FIG. 6B is a bar graph showing Tregs plotted as percentages of CD4+ T cells. 2.0 mg TGF-β IL-2 CD4-targeted nanoparticles were injected I.P. and mice were sacrificed after 5 days for FACS analysis. (*p<0.05 vs. untreated controls). FIG. 6C is dot plot showing Treg numbers per tissue in the experiment described in FIG. 6B.

DETAILED DESCRIPTION OF THE INVENTION

I. Definitions

Figure 1A:
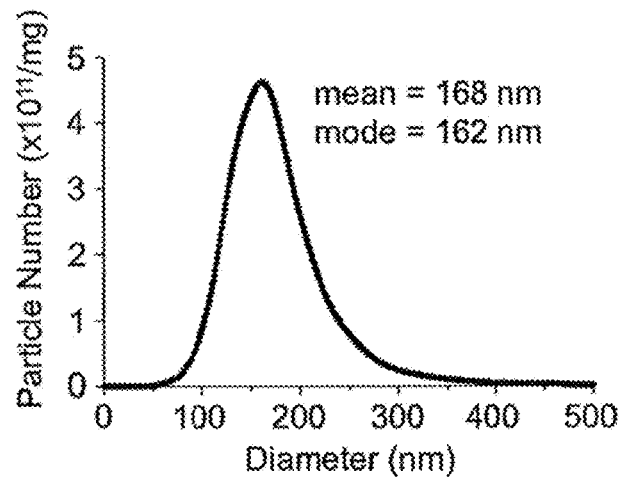
FIG. 1A is a graph showing quantification of nanoparticle size distribution by Nanosight particle tracking system.

"Small molecule," as used herein, refers to molecules with a molecular weight of less than about 2000 g/mol, more preferably less than about 1500 g/mol, most preferably less than about 1200 g/mol.

"Hydrogel," as used herein, refers to a water-swellable polymeric matrix formed from a three-dimensional network of macromolecules held together by covalent or non-covalent crosslinks, that can absorb a substantial amount of water (by weight) to form a gel.

"Nanoparticle", as used herein, generally refers to a particle having a diameter from about 10 nm up to, but not including, about 1 micron, preferably from 100 nm to about 1 micron. The particles can have any shape. Nanoparticles having a spherical shape are generally referred to as "nanospheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Active Agent", as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

Abbreviations

CD=cluster of differentiation
DMSO=dimethylsulfoxide
ELISA=enzyme-linked immunosorbent assay
FACS=fluorescent activated cell sorting
FBS=fetal bovine serum
GFP=green fluorescent protein
HCl=hydrochloric acid
mTOR=mammalian target of rapamycin
NaCl=sodium chloride
PE=phycoerythrin
PFA=paraformaldehyde
TCR=T cell receptor

II. Compositions

Compositions and methods of use thereof for delivery of growth factors needed for stable Tregs are provided. In preferred embodiments, the compositions and methods of use thereof can induce, increase, or enhance a functionally robust induced CD4 Treg population (e.g., Foxp3+ Treg, iTreg, etc., as discussed above) in-vivo.

The compositions generally include delivery vehicles including TGF-β and IL-2. Delivery vehicles include, for example, polymeric particles, silica particles, liposomes, or multilamellar vesicles. The TGF-β and IL-2 can be loaded into, attached to the surface of, and/or enclosed within the delivery vehicle into separate particles and delivered in parallel or tandem. In the most preferred embodiments, TGF-β and IL-2 are co-loaded, attached, and/or enclosed within the same delivery vehicle. Preferably, the delivery vehicles are targeted to CD4.

Nanoparticle compositions are discussed in more detail below. In preferred embodiments, the nanoparticles are composed of poly(lactic-co-glycolic) acid (PLGA). PLGA particles have been used extensively for the controlled delivery of various proteins to many cell types. PLGA is an FDA approved polymer that degrades via hydrolysis, and nanoparticles made from PLGA release encapsulated proteins over the course of several days to weeks as the polymer matrix erodes. In artificial antigen-presentation systems comprised of PLGA microparticles, sustained IL-2 release has been shown to enhance CD8 T cell proliferation and function due to local accumulation of cytokines at the immunological synapse, mimicking paracrine cytokine delivery. PLGA micro- and nanoparticles surface-conjugated with antibodies have been shown to facilitate attachment to specific cell types.

The particles can generate and maintain tunable cytokine conditions at a target cell surface. The Examples below illustrate Treg induction by CD4-targeted nanoparticles co-encapsulating TGF-β and IL-2. The experiments illustrate the CD4 cell-binding capacity of the particles and their ability to generate Tregs in-vitro and in-vivo. Nanoparticle-induced Tregs are more efficacious in both their suppressive function and demonstrate enhanced phenotypic stability in comparison to conventionally induced Tregs.

A. Nanoparticle Formation

The nanoparticles are typically formed using an emulsion process, single or double, using an aqueous and a non-aqueous solvent. Typically, the nanoparticles contain a minimal amount of the non-aqueous solvent after solvent removal. Preferred methods of preparing these nanoparticles are described in the examples.

In one embodiment, nanoparticles are prepared using emulsion solvent evaporation method. A polymeric material is dissolved in a water immiscible organic solvent and mixed with a drug solution or a combination of drug solutions. The water immiscible organic solvent is preferably a GRAS ingredient such as chloroform, dichloromethane, and acyl acetate. The drug can be dissolved in, but is not limited to, one or a plurality of the following: acetone, ethanol, methanol, isopropyl alcohol, acetonitrile and Dimethyl sulfoxide (DMSO). An aqueous solution is then added into the resulting mixture solution to yield emulsion solution by emulsification. The emulsification technique can be, but not limited to, probe sonication or homogenization through a homogenizer.

In another embodiment, nanoparticles are prepared using nanoprecipitation methods or microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The agents may be associated with the surface of, encapsulated within, surrounded by, and/or distributed throughout the polymeric matrix of the particles.

In another embodiment, nanoparticles are prepared by the self-assembly of the amphiphilic polymers, optionally including hydrophilic and/or hydrophobic polymers, using emulsion solvent evaporation, a single-step nanoprecipitation method, or microfluidic devices.

Two methods to incorporate targeting moieties into the nanoparticles include: i) conjugation of targeting ligands to the hydrophilic region (e.g. PEG) of polymers prior to nanoparticle preparation; and ii) incorporation of targeting molecules onto nanoparticles where the PEG layer on the nanoparticle surface can be cleaved in the presence of a chemical or enzyme at tissues of interest to expose the targeting molecules.

Particles may be microparticles or nanoparticles. Nanoparticles are preferred for intertissue application, penetration of cells, and certain routes of administration. The nanoparticles may have any desired size for the intended use. The nanoparticles may have any diameter from 10 nm to 1,000 nm. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 50 nm to 350 nm, from 50 nm to 300 nm, or from 50 nm to 200 nm. In preferred embodiments the nanoparticles can have a diameter less than 400 nm, less than 300 nm, or less than 200 nm.

The average diameters of the nanoparticles are typically between about 50 nm and about 500 nm, preferably between about 50 nm and about 350 nm. In some embodiments, the average diameters of the nanoparticles are about 100 nm. The zeta potential of the nanoparticles is typically between about −50 mV and about +50 mV, preferably between about −25 mV and +25 mV, most preferably between about −10 mV and about +10 my.

The following are exemplary materials and methods of making polymeric NPs.

1. Materials for Making Polymeric NPs a. Polymers

The nanoparticle can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly (hydroxy acids); poly(vinyl alcohol), and copolymers thereof.

The nanoparticle can contain one or more hydrophobic polymers. Examples of suitable hydrophobic polymers include polyhydroxyacids such as poly(lactic acid), poly (glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the hydrophobic polymer is an aliphatic polyester. In preferred embodiments, the hydrophobic polymer is poly(lactic acid), poly(glycolic acid), or poly(lactic acid-co-glycolic acid).

The nanoparticle can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydolyzable crosslinking groups to render the crosslinked polymer insoluble or sparingly soluble in water.

Biodegradable polymers in the nanoparticle can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly (ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof.

The nanoparticles can contain one or more amphiphilic polymers. Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof. In preferred embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both.

In preferred embodiments the nanoparticles contain a first amphiphilic polymer having a hydrophobic polymer block, a hydrophilic polymer block, and targeting moiety conjugated to the hydrophilic polymer block; and a second amphiphilic polymer having a hydrophobic polymer block and a hydrophilic polymer block but without the targeting moiety. The hydrophobic polymer block of the first amphiphilic polymer and the hydrophobic polymer block of the second amphiphilic polymer may be the same or different. Likewise, the hydrophilic polymer block of the first amphiphilic polymer and the hydrophilic polymer block of the second amphiphilic polymer may be the same or different.

In particularly preferred embodiments the nanoparticle contains biodegradable polyesters or polyanhydrides such as poly(lactic acid), poly(glycolic acid), and poly(lactic-co-glycolic acid). The nanoparticles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker.

The nanoparticles can also contain one or more polymer conjugates containing end-to-end linkages between the polymer and a targeting moiety or a detectable label. For example, a modified polymer can be a PLGA-PEG-peptide block polymer.

The nanoparticles can contain one or a mixture of two or more polymers. The nanoparticles may contain other entities such as stabilizers, surfactants, or lipids. The nanoparticles may contain a first polymer having a targeting moiety and a second polymer not having the targeting moiety. By adjusting the ratio of the targeted and non-targeted polymers, the density of the targeting moiety on the exterior of the particle can be adjusted.

The nanoparticles can contain an amphiphilic polymer having a hydrophobic end, a hydrophilic end, and a targeting moiety attached to the hydrophilic end. In some embodiments the amphiphilic macromolecule is a block copolymer having a hydrophobic polymer block, a hydrophilic polymer block covalently coupled to the hydrophobic polymer block, and a targeting moiety covalently coupled to the hydrophilic polymer block. For example, the amphiphilic polymer can have a conjugate having the structure A-B-X where A is a hydrophobic molecule or hydrophobic polymer, preferably a hydrophobic polymer, B is a hydrophilic molecule or hydrophilic polymer, preferably a hydrophilic polymer, and X is a targeting moiety. Preferred amphiphilic polymers include those where A is a hydrophobic biodegradable polymer, B is PEG, and X is a targeting moiety that targets, binds, and/or adheres to a target.

In some embodiments the nanoparticle contains a first amphiphilic polymer having the structure A-B-X as described above and a second amphiphilic polymer having the structure A-B, where A and B in the second amphiphilic macromolecule are chosen independently from the A and B in the first amphiphilic macromolecule, although they may be the same.

b. Active Agents

The particles are typically loaded with TGF-β and/or IL-2. In some embodiments, the particles include one or more additional active agents.

i. TGF-β

Transforming growth factor beta (TGF-β, TGF-β1, TGF-beta, etc.) is a polypeptide member of the transforming growth factor beta superfamily of cytokines. It is a secreted protein that performs many cellular functions, including the control of cell growth, cell proliferation, cell differentiation and apoptosis. TGF-β can promote either T-helper 17 cells (Th17) or regulatory T-cells (Treg) lineage differentiation in a concentration-dependent manner At high concentrations, leads to FOXP3-mediated suppression of RORC and down-regulation of IL-17 expression, favoring Treg cell development.

Nucleic acid and protein sequences for TGF-β are known in the art. See, for example, UniProtKB—P01137 (TGFB1_HUMAN) and the amino acid sequence provided therein (P01137-1: Length:390 Mass (Da):44,341, Last modified: Feb. 1, 1991-v2) and Human mRNA for transforming growth factor-beta (TGF-beta) GenBank: X02812.1 GI:37092 and the mRNA and amino acid sequences provided there, all the forgoing of which is specifically incorporated by reference in its entirety.

ii. IL-2

Interleukin-2 (IL-2) is an interleukin cytokine signaling molecule. IL-2 has important roles in immune function, tolerance and immunity, primarily via its direct effects on T cells. In the thymus, it prevents autoimmune diseases by promoting the differentiation of certain immature T cells into regulatory T cells, which suppress other T cells that are otherwise primed to attack normal healthy cells in the body. Nucleic acid and protein sequences for IL-2 are known in the art. See, for example, UniProtKB—P60568 (IL2_HUMAN) and the amino acid sequence provided therein (P60568-1: Length:153 Mass (Da):17,628 Last modified: Jul. 21, 1986-v1) and Human mRNA encoding interleukin-2 (IL-2) a lymphozyte regulatory molecule GenBank: V00564.1 GI:33780 and the mRNA and amino acid sequences provided there, all the forgoing of which is specifically incorporated by reference in its entirety.

iii. Additional Active Agents

In some embodiments, the same or different particles include additional active agents. Additional active agents to be delivered include therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound. Exemplary therapeutic agents that can be incorporated into, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals, anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides) to activate the innate immune system, molecules that mobilize and optimize the adaptive immune system, molecules that activate or up-regulate suppressor or regulatory T-cells, agents that promote uptake of particles into cells, nutraceuticals such as vitamins, and oligonucleotide drugs (including DNA, RNAs, antisense, aptamers, small interfering RNAs, ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

In certain embodiments, the particles include one or more immunomodulatory agents. Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

c. Moieties attached to Particles

The surface of the particles can be modified to facilitate targeting through the attachment of targeting molecules and other ligands. These can be proteins, peptides, nucleic acid molecules, lipids, saccharides or polysaccharides that bind to a receptor or other molecule on the surface of a targeted cell. The degree of specificity can be modulated through the selection of the targeting molecule. For example, antibodies are very specific. The targeting moiety of the nanoparticle can be an antibody or antigen binding fragment thereof. These can be polyclonal, monoclonal, fragments, recombinant, or single chain, many of which are commercially available or readily obtained using standard techniques. T-cell specific molecules can be bound to the surface of the particle. The targeting molecules may be conjugated to the terminus of one or more PEG chains present on the surface of the particle.

The targeting moieties should can have an affinity for a cell-surface receptor or cell-surface antigen on the target cells. The targeting moieties may result in internalization of the particle within the target cell.

The degree of specificity with which the particles are targeted can be modulated through the selection of a targeting molecule with the appropriate affinity and specificity. For example, a targeting moiety can be a polypeptide, such as an antibody that specifically recognizes an immune cell marker such as CD4.

CD4 (cluster of differentiation 4) is a glycoprotein found on the surface of immune cells such as T helper cells, monocytes, macrophages, and dendritic cells. Like many cell surface receptors/markers, CD4 is a member of the immunoglobulin superfamily. It has four immunoglobulin domains (D1 to D4) that are exposed on the extracellular surface of the cell: D1 and D3 resemble immunoglobulin variable (IgV) domains, while D2 and D4 resemble immunoglobulin constant (IgC) domains CD4 uses its D1 domain to interact with the β2-domain of MHC class II molecules. T cells expressing CD4 molecules (and not CD8) on their surface, therefore, are specific for antigens presented by MHC II and not by MHC class I (they are MHC class II-restricted). MHC class I contains Beta-2 microglobulin. The short cytoplasmic/intracellular tail (C) of CD4 contains a special sequence of amino acids that allow it to interact with the Ick molecule.

Nucleic acid and protein sequences for CD4 are known in the art. See, for example, UniProtKB—P01730 (CD4_HUMAN) and the amino acid sequence provided therein (P01730-1: Length:458, Mass (Da):51,111, Last modified: Nov. 1, 1988-v1) and Human T-cell surface glycoprotein T4 mRNA, complete cds GenBank: M12807.1 GI:179141 and the mRNA and amino acid sequences provided there, all the forgoing of which is specifically incorporated by reference in its entirety.

In preferred embodiments, the targeting moiety targets an extracellular portion of CD4. The domains of CD4 are known in the art. See, for example, UniProtKB—P01730, which provides the following domain structure:

| Feature key | Position(s) | Length | Description |
| --- | --- | --- | --- |
| Topological domain$^i$ | 26-396 | 371 | Extracellular |
| Transmembrane$^i$ | 397-418 | 22 | Helical |
| Topological domain$^i$ | 419-458 | 40 | Cytoplasmic |

Some embodiments include one or more additional targeting moieties. Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer*, 2:83-90 (2002). The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Targeting molecules can also include neuropilins and endothelial targeting molecules, integrins, selectins, and adhesion molecules. Targeting molecules can be covalently bound to particles using a variety of methods known in the art.

Exemplary types of targeting moieties that can be used to target CD4 and/or other targets are discussed below.

i. Peptide Targeting Moieties

In a preferred embodiment, the targeting moiety is a peptide. The targeting peptides can be covalently associated with the polymer and the covalent association can be mediated by a linker. The peptides target to actively growing (angiogenic) vascular endothelial cells. Those angiogenic endothelial cells frequently appear in metabolic tissues such as adipose tissues.

ii. Antibody Targeting Moieties

The targeting moiety can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc.

Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')$_2$, dsFv, sFv, diabodies, and triabodies. In certain embodiments, the antibody is a single chain antibody.

iii. Aptamer Targeting Moieties

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

c. Additional Moieties

The particles can contain one or more polymer conjugates containing end-to-end linkages between the polymer and a moiety. The moiety can be a targeting moiety, a detectable label, or a therapeutic, prophylactic, or diagnostic agent. For example, a polymer conjugate can be a PLGA-PEG-phosphonate. The additional targeting elements may refer to elements that bind to or otherwise localize the nanoparticles to a specific locale. The locale may be a tissue, a particular cell type, or a subcellular compartment. The targeting element of the nanoparticle can be an antibody or antigen binding fragment thereof, an aptamer, or a small molecule (less than 500 Daltons). The additional targeting elements may have an affinity for a cell-surface receptor or cell-surface antigen on a target cell and result in internalization of the particle within the target cell.

In some embodiments, a cell penetrating peptide, also known as cell permeable peptides, protein transduction domains (PTDs), membrane translocating sequences (MTSs) and Trojan peptides, (for example a stuimulus-responsive cell penetrating peptide) is a conjugated to the particle. Cell penetrating peptides include, but are not limited to, virus-derived or mimicking polymers such as TAT, influenza fusion peptide, rabies virus glycoprotein fragment (RVG), neuropilin, penetratin, and polyarginines. Anaspec has commercially available CPPs.

d. Imaging Agents

The particles can also contain a detectable label, such as a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. These may be encapsulated within, dispersed within, or conjugated to the polymer.

For example, a fluorescent label can be chemically conjugated to a polymer of the nanoparticle to yield a fluorescently labeled polymer. In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine and barium.

2. Methods of Making Particles a. Polymer Conjugates

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization.

In some embodiments an amphiphilic polymer is synthesized starting from a hydrophobic polymer terminated with a first reactive coupling group and a hydrophilic polymer terminated with a second reactive coupling group capable of reacting with the first reactive coupling group to form a covalent bond. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In preferred embodiments a hydrophobic polymer terminated with an amine or an amine-reactive linking group is coupled to a hydrophilic polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer terminated with a primary amine, such as a PEG-NH$_2$ to form an amphiphilic PLGA-b-PEG block copolymer.

In some embodiments a conjugate of an amphiphilic polymer with a targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a targeting moiety having a reactive group that is complimentary to the first reactive group to form a covalent bond between the hydrophilic polymer and the targeting moiety. The protective group can then be removed to provide a second reactive coupling group, for example to allow coupling of a hydrophobic polymer block to the conjugate of the hydrophilic polymer with the targeting moiety. A hydrophobic polymer terminated with a reactive coupling group complimentary to the second reactive coupling group can then be covalently coupled to form the conjugate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments a conjugate is formed having a moiety conjugated to both ends of the amphiphilic polymer. For example, an amphiphilic polymer having a hydrophobic polymer block and a hydrophilic polymer block may have targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a targeting moiety having a reactive coupling group complimentary to the second reactive coupling group, thereby forming a conjugate of the hydrophilic polymer to the targeting moiety. The first protective group and the second protective group can be removed to yield a pair of complimentary reactive coupling groups that can be reacted to covalently link the hydrophobic polymer block to the hydrophilic polymer block.

b. Emulsion Methods

In some embodiments, a multimodal nanoparticle is prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or a more of the following: PPARgamma activators (e.g. Rosiglitazone, (RS)-5-[4-(2-[methyl(pyridin-2-yl)amino] ethoxy)benzyl]thiazolidine-2,4-dione, Pioglitazone, (RS)-5-(4-[2-(5-ethylpyridin-2-yl)ethoxy]benzyl)thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostagladin E2 analog (PGE2, (5Z,11α,13E,15S)-7-[3-hydroxy-2-(3-hydroxyoct-1-enyl)-5-oxo-cyclopentyl]hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), Fibroblast Growth Factor 21 (FGF-21), Irisin, RNA, DNA, chemotherapeutic compounds, nuclear magnetic resonance (NMR) contrast agents, or combinations thereof. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO).

In some embodiments the polymer solution contains one or more polymer conjugates as described above. The polymer solution can contain a first amphiphilic polymer conjugate having a hydrophobic polymer block, a hydrophilic polymer block, and a targeting moiety conjugated to the hydrophilic end. In preferred embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the targeting moieties can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer. The plaque-targeted peptides or fluorophores or drugs may be associated with the surface of, encapsulated within, surrounded by, and/or distributed throughout the polymeric matrix of this inventive particle.

c. Nanoprecipitation Method

In another embodiment, a multimodal nanoparticle is prepared using nanoprecipitation methods or microfluidic devices. A polymeric material is mixed with a drug or drug combinations in a water miscible organic solvent. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or more of the following: PPARgamma activators (e.g. Rosiglitazone, (RS)-5-[4-(2-[methyl(pyridin-2-yl)amino] ethoxy)benzyl]thiazolidine-2,4-dione, Pioglitazone, (RS)-5-(4-[2-(5-ethylpyridin-2-yl)ethoxy]benzyl)thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostagladin E2 analog (PGE2, (5Z,11α,13E,15S)-7-[3-hydroxy-2-(3-hydroxyoct-1-enyl)-5-oxo-cyclopentyl]hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), RNA, DNA, chemotherapeutic compounds, nuclear magnetic resonance (NMR) contrast agents, or combinations thereof. The water miscible organic solvent, can be, but is not limited to, one or more of the following: acetone, ethanol, methanol, isopropyl alcohol, acetonitrile and Dimethyl sulfoxide (DMSO). The resulting mixture solution is then added to a polymer non-solvent, such as an aqueous solution, to yield nanoparticle solution. The plaque-targeted peptides or fluorophores or drugs may be associated with the surface of, encapsulated within, surrounded by, and/or distributed throughout the polymeric matrix of this inventive particle.

d. Microfluidics

Methods of making nanoparticles using microfluidics are known in the art. Suitable methods include those described in U.S. Patent Application Publication No. 2010/0022680 A1 by Karnik et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

e. Other Methodologies

Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

Hot Melt Microencapsulation.

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000.

Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

Spray-Drying.

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15 □C, aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

Hydrogel Microparticles.

Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

3. Methods of Encapsulating or Attaching Molecules to the Surface of the Particles There are two principle groups of molecules to be encapsulated or attached to the polymer, either directly or via a coupling molecule: targeting molecules, attachment molecules and therapeutic, nutritional, diagnostic or prophylactic agents. These can be coupled using standard techniques. The targeting molecule or therapeutic molecule to be delivered can be coupled directly to the polymer or to a material such as a fatty acid which is incorporated into the polymer.

Functionality refers to conjugation of a ligand to the surface of the particle via a functional chemical group (carboxylic acids, aldehydes, amines, sulfhydryls and hydroxyls) present on the surface of the particle and present on the ligand to be attached. Functionality may be introduced into the particles in two ways.

The first is during the preparation of the microparticles, for example during the emulsion preparation of microparticles by incorporation of stablizers with functional chemical groups.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after prepartion. This second class also includes a process whereby amphiphilic molecules such as fatty acids, lipids or functional stabilizers may be passively adsorbed and adhered to the particle surface, thereby introducing functional end groups for tethering to ligands.

B. Pharmaceutical Compositions

Pharmaceutical compositions including particles are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the particles to the immediate area of the implant.

The particles can be provided to the cell either directly, such as by contacting it with the cell, or indirectly, such as through the action of any biological process. For example, the particles can be formulated in a physiologically acceptable carrier or vehicle, and injected into a tissue or fluid surrounding the cell. The particles can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the particle-associated active agent administered to an individual will be less than the amount of the unassociated active agent that must be administered for the same desired or intended effect.

1. Formulations for Parenteral Administration

In a preferred embodiment the particles are administered in an aqueous solution, by parenteral injection. The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The particles can be applied topically. Topical administration can include application to the lungs, nasal, oral (sublingual, buccal), vaginal, or rectal mucosa. These methods of administration can be made effective by formulating the shell with transdermal or mucosal transport elements. For transdermal delivery such elements may include chemical enhancers or physical enhancers such as electroporation or microneedle delivery. For mucosal delivery PEGylation of the outer shell or addition of chitosan or other mucosal permeants or PH protective elements for oral delivery.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkeiines and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al. *Biomaterials*. 29(6): 703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

III. Methods of Use

A. Treatment Strategy

As discussed in more detail below, the disclosed compositions and methods are particularly useful in the context of immune suppression and induction and maintenance of immune tolerance. By efficiently delivering both TGF-β and IL-2 to CD4 T cells, this platform circumvents several fundamental drawbacks of today's leading autoimmune therapies. Paracrine cytokine delivery can 1) increase Treg induction signaling in-vitro and in-vivo, 2) enhance suppressive function, 3) retained Foxp3 expression even in depolarizing conditions, or combinations thereof.

Functional Tregs are critical for maintaining self-tolerance and preventing autoimmunity, but effective therapies that harness Treg function remain elusive. The Examples below demonstrate that biodegradable nanoparticles can enhance the ability of combination TGF-β and IL-2 to generate functional and stable Tregs.

Administration of regulatory cytokines to treat autoimmune pathologies has proven to be a promising strategy. Specifically, the administration of low-dose recombinant IL-2 can reverse type 1 diabetes in NOD mice by expanding natural Treg numbers. In humans, IL-2 therapy has achieved clinical benefit in a small number of patients with graft-versus-host disease or vasculitis. Drawbacks to this approach arise from the pleiotropic nature of IL-2, which also induces proliferation of natural killer cells and CD8 effector T cells. Additionally, recombinant IL-2 has a short half-life in circulation, requiring frequent doses to maintain its affect while minimizing off-target signaling. One strategy to overcome IL-2 induced lymphocyte proliferation involves the co-administration of suppressive drugs such as rapamycin. While rapamycin is thought to work primarily by inhibiting IL-2-mediated proliferation specifically in T effector cells, it also induces TGF-β production in lymphocytes. Rapamycin/IL-2 therapy indeed prevented effector T cell proliferation in a clinical trial, but both natural killer cell and eosinophil numbers were enhanced, and beta cell function declined. These adverse effects reflected toxicity associated with systemic mTOR inhibition and off-target IL-2 signaling. The disclosed nanoparticles compositions and methods of use thereof directly deliver both IL-2 and TGF-β to T cells, bypassing systemic toxicity.

In some embodiments, nanoparticles are loaded with a ratio (1:2) of IL-2:TGF-β targeted to CD4 cells and can signal cooperatively at the cell surface. TGF-β, a regulatory cytokine recognized as a Treg inducer, can be used in conjunction with IL-2 to generate CD4 Tregs in-vitro. The Examples below show that the efficiency of Treg induction after incubation with TGF-β and IL-2 was maintained after prior depletion of nTregs, showing that the cytokine combination can induce the differentiation of naïve Foxp3– CD4 T cells. Thus in some embodiments, the particles are administered in an effective amount to induce the differentiation of naïve Foxp3– CD4 T cells.

It is believed that sustained release of both cytokines illustrated in the Examples below was comparable due to physiochemical similarities between both proteins. To verify preservation of each cytokine's structure following PLGA encapsulation and particle synthesis, bioactivity was assayed during particle-mediated release. Encapsulated cytokines displayed greater bioactivity compared to soluble counterparts. Enhanced bioactivity may be due to increased local concentration gradients, and this has been observed with encapsulated IL-2. Strikingly, with encapsulated TGF-β, not only was the signaling threshold reduced, but the Foxp3 induction plateau was increased, highlighting the impact of high local concentration gradients.

Thus, the nanoparticle-mediated paracrine-delivery of IL-2 and TGF-β may be more effective at driving naïve CD4 cells to become Tregs. For example, paracrine signaling reveals that diffusive cytokine transfer may trigger signaling outcomes through reorganization of membrane receptors. Thus in some embodiments, the particles are administered in an effective amount to induce naïve CD4 cells to become Tregs. TGF-β signaling requires surface dimerization of two receptor subunits, which may partially depend on this paracrine affect, leading to the observed enhancement by nanoparticle-mediated delivery.

In addition to more efficient generation of Foxp3+ Tregs, the Examples illustrate that nanoparticles induce Tregs that are more effective suppressors on a per cell basis. When Foxp3+ Treg cell numbers were matched between soluble cytokine-induced suppressors and nanoparticle-generated suppressors, nanoparticle-induced suppressors showed superior ability to inhibit CD4 effector proliferation in response to TCR ligation and costimulation. This effect was retained down to 1/32 initial Treg fraction, and verified that nanoparticle binding to the Treg cell surface had no detrimental impact on their functional capacity, but facilitated enhanced function. In these experiments, nanoparticle-induced suppressor cells retained Foxp3 expression to a greater extent than soluble cytokine-induced suppressor cells, which showed no correlation between initial Treg fraction and final Foxp3 expression. This observation supports the conclusion that nanoparticle-mediated delivery of TGF-β and IL-2 blocks the loss of Foxp3 expression over time. Thus in some embodiments, the particles are administered in an effective amount to reduce the loss of Foxp3 expression over time.

Results of the Foxp3 kinetic assays exemplified below indicate that nanoparticle-mediated delivery of TGF-β and IL-2 may also help overcome T cell plasticity in the context of inflammation and typically observed with Treg cell therapy. Although adoptive transfer of ex-vivo induced Tregs are effective at treating diabetes in NOD mice, a growing body of work indicates that these cells can turn off Foxp3 expression and even revert to an effector phenotype within inflammatory environments. Nanoparticle delivery can maintain local cytokine availability to targeted cells even within polarizing microenvironments, which is useful for maintenance of Foxp3 expression in the absence of endogenous regulatory factors.

The Examples also illustrate that systemic administration of CD4-targeted nanoparticles results in accumulation, in secondary lymphoid tissues, making encapsulated cytokines available during T cell differentiation. Indeed, systemic administration of CD4-targeted TGF-β+IL-2 nanoparticles enhances Treg frequency in these tissues.

B. Methods of Treatment

The disclosed methods typically include using CD4-targeted particles loaded with TGF-β+IL-2, to deliver the cytokines into cells, or to a cell's microenvironment. The methods typically include contacting the TGF-β+IL-2 agent-loaded particles with one more cells. The contacting can occur in vivo or in vitro. The compositions can be administered to the subject therapeutically or prophylactically. Exemplary therapeutic and prophylactic strategies are discussed in more detail below and in the Examples.

Immune cells, preferably T cells, can be contacted in vivo or ex vivo with TGF-β+IL-2-loaded particles to decrease or inhibit immune responses including, but not limited to inflammation. The T cells can include any cell which express the T cell receptor, including α/β and γ/δ T cell receptors. T-cells include all cells which express CD3, including T-cell subsets which also express CD4 and CD8. T-cells include both naïve and memory cells and effector cells such as CTL. T-cells also include regulatory cells such as Th1, Tc1, Th2, Tc2, Th3, Th17, Th22, Treg, and Tr1 cells. T-cells also include NKT-cells and similar unique classes of the T-cell lineage. In some embodiments, the cells express or are induced to express CD4+, Foxp3+, CD25+, or any combination thereof.

In the most preferred embodiments, the particles are contacted with (1) Treg in an effective amount to induce, enhance, or maintain a regulatory phenotype or a combination thereof, (2) effector T cells in an effective amount to reduce effector function, induce transdifferentiation into a Treg, or a combination thereof; or a combination of (1) and (2). In some embodiments, the methods increase the number of Tregs, for example, percentage of Tregs in a total CD4+ population. In some embodiments, the number or ratio of Foxp3+ Tregs in increased. In some embodiments, the number or ratio (relative to total CD4+) of effector cells is reduced or not increased.

For example, the compositions be used to increase or promote the activity of Tregs, increase the production of cytokines such as IL-10 from Tregs, increase the differentiation of Tregs, increase the number of Tregs, or increase the survival of Tregs. The compositions can be used to directly or indirectly modulate Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs.

In some embodiments, the disclosed compositions are administered in combination with a second therapeutic. Combination therapies may be useful in immune modulation. In some embodiments, the compositions can be used to attenuate or reverse the activity of a pro-inflammatory drug, and/or limit the adverse effects of such drugs.

Administration of a drug or other cargo to cells or a subject using particles can be compared to a control, for example, delivery of the TGF-β, IL-2 and/or other cargo to cells or a subject using conventional delivery methods such as free cargo/drug delivery, or delivery using conventional liposomal methods such as LIPOFECTAMINE®. Particles can be used to deliver cargo to target cells with increased efficacy compared to conventional delivery methods. In some embodiments less cargo or drug is required when delivered using particles compared to conventional delivery methods to achieve the same or greater therapeutic benefit.

In some embodiments toxicity is reduced or absent compared to conventional delivery methods. For example, in some embodiments, white blood cell, platelet, hemoglobin, and hematocrit levels were within normal physiological ranges; no liver or renal toxicities are observed; body weight and serum concentrations for alkaline phosphatase, alanine transferase, total bilirubin, and blood urea nitrogen are normal; or combinations thereof following administration of loaded particles to the subject.

1. In Vivo Methods

The disclosed compositions can be used in a method of delivering active agents to cells in vivo. In some in vivo approaches, the compositions are administered to a subject in a therapeutically effective amount. As used herein, the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. In some embodiments, the subject has inflammation, an inflammatory disease or disorder, an autoimmune, or is a subject for or a recipient of transplantation, as discussed in more detail below.

a. Drug Delivery

The particles can be used to deliver an effective amount of TGF-β and IL-2 alone or in combination with one or more therapeutic, diagnostic, and/or prophylactic agents to an individual in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles may be administered as a dry powder, as an aqueous suspension (in water, saline, buffered saline, etc), in a hydrogel, organogel, in capsules, tablets, troches, or other standard pharmaceutical excipient An exemplary embodiment is a dry powder rehydrated with the capsulant of interest in sterile saline or other pharmaceutically acceptable excipient.

As discussed herein, compositions can be used to as delivery vehicles for a number of active agents including small molecules, nucleic acids, proteins, and other bioactive agents. The active agent or agents can be encapsulated within, dispersed within, and/or associated with the surface of the particle. In some embodiments, the particle packages two, three, four, or more different active agents for simultaneous delivery to a cell.

b. Transfection

The disclosed compositions can be for cell transfection of polynucleotides. For example, in some embodiments, the TGF-β and IL-2 are delivered as a polynucleotide (e.g., mRNA or a vector, etc., encoding the TGF-β+IL-2) that can be expressed by the cells upon transfection. In some embodiments, other polynucleotides are utilized as part of the therapy. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000.

Polynucleotides delivered by the particles can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. The polynucleotides expresses or induce expression of TGF-β and/or IL-2 in cells.

In some embodiments two or more polynucleotides are administered in combination. Thus TGF-β and IL-2 can be co-delivered with other polynucleotide drugs. In some embodiments, the polynucleotide encodes a protein. Exemplary proteins include, for example, (a) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor-α, hepatocyte growth factor and insulin-like growth factor; (b) cell cycle inhibitors such as cyclin-dependent kinases, thymidine kinase ("TK"), and other agents useful for interfering with cell proliferation; (c) bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. BMPs are typically dimeric proteins that can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the particles are used to deliver mRNA or non-integrating expression vectors that are expressed transiently in the host cell.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

2. In Vitro Methods

The disclosed compositions can be used in a method of delivering active agents to cells in vitro. For example, the compositions can be used to induce, expand, or enhance Treg numbers, suppressive effect, or stabilize Foxp3 expression ex vivo, for use, for example in Treg therapy. In some embodiments, TGF-β+IL-2 is delivered to the cells in an effective amount to change the genotype or a phenotype of the cell. Thus the compositions can be used in methods of Adoptive Cell Transfer (ACT). ACT refers to the transfer of cells into a patient. As discussed in more detail below, cells can originated from the patient and treated ex vivo before being transferred back. They can also originate from another individual. The cells are most commonly derived from the immune system, with the goal of transferring improved immune functionality and characteristics along with the cells back to the patient. In some embodiments, the subject has inflammation, an inflammatory disease or disorder, an autoimmune, or is a subject for or a recipient of transplantation, as discussed in more detail below.

The disclosed compositions and methods are particular useful in the context of adoptive Treg therapy. Applications for Treg therapy are known in the art and include, for example, treatment of inflammation, autoimmune disease, graft rejection and other conditions discussed herein and known in the art. See, for example, Nagahama, et al., *Methods Mol* 2007; 380:431-42, which discusses that CD4+ CD25+ regulatory T (Treg) cells can be exploited to establish immunologic tolerance to allogeneic transplants.

The cells can be primary cells isolated from a subject, or cells of an established cell line. The cells can be of a homogenous cell type, or can be a heterogeneous mixture of different cells types. For example, the particles can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture.

The methods are particularly useful in the field of personalized therapy, for example to de-differentiate cells, transdifferentiate cells, differentiate cells, reprogram cells, enhance or prolong the function of cells, and/or reduce or prevent the de-differentiation, transdifferentiation, or differentiation of cells. For example, target cells are first isolated from a donor using methods known in the art, contacted with the particle including TGF-β+IL-2 causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration. For examples, in some embodiments the disclosed methods are be used to change the phenotype of immune cells.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use.

C. Diseases to Be Treated

1. Inflammatory Responses

A preferred embodiment provides methods for treating or alleviating one or more symptoms of inflammation. In some embodiments, the compositions and methods disclosed are useful for treating chronic and persistent inflammation. Inflammation in general can be treated using the disclosed TGF-β+IL-2-loaded particles.

An immune response including inflammation can be inhibited or reduced in a subject, preferably a human, by administering an effective amount of TGF-β+IL-2-loaded particles to inhibit or reduce the biological activity of an immune cell or to reduce the amounts of proinflammatory molecules at a site of inflammation. Exemplary proinflammatory molecules include, but are not limited to, IL-1β, TNF-α, TGF-beta, IFN-γ, IL-17, IL-6, IL-23, IL-22, IL-21, and MMPs.

TGF-β+IL-2-loaded particles can cause Tregs to have an enhanced suppressive effect on an immune response. Tregs can suppress differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. For example, TGF-β+IL-2-loaded particles can cause Tregs to have an enhanced suppressive effect on Th1 and/or Th17 cells to reduce the level of IFN-γ and IL-17 produced, respectively. TGF-β+IL-2-loaded particles can cause Tregs to promote or enhance production of IL-10 to suppress the Th1 and Th17 pathway, or to increase the number of Tregs.

The TGF-β+IL-2-loaded particles can also be administered to a subject in an amount effective to increase Treg cell populations or numbers or ratios relative to other cell types. In some embodiments, the TGF-β+IL-2-loaded particles increases the population or number or ratio of Fox3P+ Tregs, for example, relative to total CD4+ cells.

In some embodiments, IL-10 and/or TGF-β production by Tregs is increased relative to a control by contacting the Tregs with an effective amount of TGF-β+IL-2-loaded particles. The increase can occur in vitro or in vivo.

Administration is not limited to the treatment of existing conditions, diseases or disorders (i.e. an existing inflammatory or autoimmune disease or disorder) but can also be used to prevent or lower the risk of developing such diseases in an individual, i.e., for prophylactic use. Potential candidates for prophylactic vaccination include individuals with a high risk of developing an inflammatory or autoimmune disease or disorder, i.e., with a personal or familial history of certain types of autoimmune disorders.

The compositions can be administered to subject in need thereof in an amount effective to treat an inflammatory or autoimmune disease or disorder. Representative inflammatory or autoimmune diseases and disorders that may be treated using TGF-β+IL-2-loaded particles include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

2. Transplant Rejection

A preferred embodiment provides methods for reducing or inhibiting transplant rejection in a subject, preferably a human subject. Transplant rejection can be inhibited or reduced in a subject by administering an effective amount of TGF-β+IL-2-loaded particles to inhibit or reduce the biological activity of an immune cell or to reduce the amounts of proinflammatory cytokines or other molecules associated with or that promote inflammation at a site of transplant. Exemplary proinflammatory molecules include, but are not limited to IL-1β, TNF-α, TGF-beta, IFN-γ, IL-17, IL-6, IL-23, IL-22, IL-21, and MMPs.

Administration is not limited to the treatment of existing conditions, diseases or disorders (i.e. an existing inflammatory or autoimmune disease or disorder) but can also be used to prevent or lower the risk of developing such diseases in an individual, i.e., for prophylactic use. Thus, the disclosed composition can be administered prior to transplant, during transplant, and after transplant.

The transplanted material can be cells, tissues, organs, limbs, digits or a portion of the body, preferably the human body. The transplants are typically allogenic or xenogenic. The disclosed compositions are administered to a subject in an effective amount to reduce or inhibit transplant rejection. Particles can be administered systemically or locally by any acceptable route of administration. In some embodiments, the compositions are administered to a site of transplantation prior to, at the time of, or following transplantation. In one embodiment, the particles are administered to a site of transplantation parenterally, such as by subcutaneous injection.

In other embodiments, particles are administered directly to cells, tissue or organ to be transplanted ex vivo. In one embodiment, the transplant material is contacted with TGF-β+IL-2-loaded particles prior to transplantation, after transplantion, or both.

In other embodiments, TGF-β+IL-2-loaded particles are administered to immune tissues or organs, such as lymph nodes or the spleen.

The transplant material can be treated with enzymes or other materials that remove cell surface proteins, carbohydrates, or lipids that are known or suspected in being involved with immune responses such as transplant rejection.

a. Cells

Populations of any types of cells can be transplanted into a subject. The cells can be homogenous or heterogenous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above. Such treatment includes transfecting the cells ex vivo with particles loaded with TGF-β+IL-2 or a nucleic acid construct enabling the cells to express TGF-β+IL-2 in vitro and in vivo.

Exemplary cells that can be transplanted include, but are not limited to, islet cells, hematopoietic cells, muscle cells, cardiac cells, neural cells, embryonic stem cells, adult stem cells, T cells, lymphocytes, dermal cells, mesoderm, endoderm, and ectodeini cells.

b. Tissues

Any tissue can be used as a transplant. Exemplary tissues include skin, adipose tissue, cardiovascular tissue such as veins, arteries, capularies, valves; neural tissue, bone marrow, pulmonary tissue, ocular tissue such as corneas and lens, cartilage, bone, and mucosal tissue.

c. Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of a TGF-β+IL-2-loaded particles to inhibit or reduce chronic transplant rejection relative to a control.

3. Graft-Versus-Host Disease (GVHD)

The disclosed TGF-β+TL-2-loaded particles can also be used to treat graft-versus-host disease (GVHD) by administering an effective amount of the composition to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

4. Diabetes

The TGF-β+IL-2-loaded particles can also be used to treat diabetes. The method includes transplanting insulin producing cells in a subject and administering to the subject an effective amount of TGF-β+IL-2-loaded particles to reduce or inhibit transplant rejection. Preferably the insulin producing cells are beta cells or islet cells. In certain embodiments, the insulin producing cells are recombinant cells engineered to produce insulin.

The insulin producing cells can be encapsulated within a matrix, such as a polymeric matrix, using suitable polymers, including, but not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof.

D. Combination Therapy

The disclosed compositions can be used alone or in combination with additional therapeutic agents. The additional therapeutic agents include, but are not limited to, immunosuppressive agents (e.g., antibodies against other lymphocyte surface markers (e.g., CD40, alpha-4 integrin) or against cytokines), other fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e. Endoxan®, Cytoxan®, Neosar®, Procytox®, Revimmune™), methotrexate (MTX) (i.e. Rheumatrex®, Trexall®), belimumab (i.e. Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

In a preferred embodiment, the additional therapeutic agent functions to inhibit or reduce T cell activation and cytokine production through a separate pathway. In one such embodiment, the additional therapeutic agent is a CTLA-4 fusion protein, such as CTLA-4 Ig (abatacept). CTLA-4 Ig fusion proteins compete with the co-stimulatory receptor, CD28, on T cells for binding to CD80/CD86 (B7-1/B7-2) on antigen presenting cells, and thus function to inhibit T cell activation. In a preferred embodiment, the additional therapeutic agent is a CTLA-4-Ig fusion protein known as belatacept. Belatacept contains two amino acid substitutions (L104E and A29Y) that markedly increase its avidity to CD86 in vivo. In another embodiment, the additional therapeutic agent is Maxy-4.

In another embodiment, the second therapeutic agent preferentially treats chronic transplant rejection or GvHD, whereby the treatment regimen effectively targets both acute and chronic transplant rejection or GvHD. In a preferred embodiment the second therapeutic is a TNF-α blocker.

In another embodiment, the second therapeutic agent increases the amount of adenosine in the serum, see, for example, WO 08/147482. In a preferred embodiment, the second therapeutic is CD73-Ig, recombinant CD73, or another agent (e.g. a cytokine or monoclonal antibody or small molecule) that increases the expression of CD73, see for example WO 04/084933. In another embodiment the second therapeutic agent is Interferon-beta.

In a preferred embodiment, the compositions are used in combination or succession with compounds that increase Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof. Antibodies to other proinflammatory molecules can also be used in combination or alternation with the TGF-β+IL-2-loaded particles. Preferred antibodies bind to IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; U.S. Pat. Nos. 5,567,709; 5,559, 112; 5,530,006; 5,484,790; 5,385,908; 5,202,332; 5,162, 333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufcnamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The present invention will be further understood by reference to the following non-limiting examples.

EXAMPLES

McHugh, et al., "Paracrine co-delivery of TGF-β and IL-2 using CD4-targeted nanoparticles for induction and maintenance of regulatory T cells," *Biomaterials*, 59:172-81 (2015). doi:10.1016/j.biomaterials.2015.04.003. Epub 2015 May 15, is specifically incorporated by references herein in its entirety.

Example 1: Nanoparticle Fabrication and Characterization Materials and Methods Nanoparticle Synthesis Human recombinant TGF-β1 (mammalian-derived, Peprotech, Rocky Hill, N.J.) and human recombinant IL-2 (Proleukin) was encapsulated in avidin-coated PLGA nanoparticles using a water/oil/water emulsion technique as previously described (35). Briefly, 2.5 µg of aqueous cytokine solution was added drop-wise while vortexing to 50 mg PLGA (50:50 monomer ratio, Durect Corp) in 3 mls chloroform. The resulting emulsion was added dropwise to 3 mls of water containing 3% poly-vinyl alcohol (Sigma-Aldrich) and 0.625 mg/ml avidin-palmitate conjugate (previously described elsewhere (35)). This double emulsion was then sonicated to create nano-sized droplets of chloroform containing encapsulated cytokine, within aqueous surfactant. Solvent was removed by magnetic stirring at room temperature for 3 hours. Hardened nanoparticles were then washed 3 times in MilliQ water and lyophilized for long-term storage. Nanoparticles were prepared fresh from lyophilized stocks for each experiment. Briefly, nanoparticles were dispersed in PBS at 10 mg/ml by vortexing and 2-3 seconds of bath sonication. CD4-targeted nanoparticles were formed by reacting avidin-coated nanoparticles in PBS with 2 µg biotin-anti-CD4 (RM 4-5, eBiosciences) per mg NP for 15 minutes and used immediately.

Characterization of Nanoparticle Size and Morphology

Nanoparticle morphology was analyzed via scanning electron microscopy (SEM). Samples were sputter-coated with gold using a Dynavac Mini Coater and imaged with a Hitachi SU-70 SEM with an accelerating voltage of 5 kV. Particle size was quantified using the Nanosight particle tracking system (NanoSight, Ltd., Wiltshire, UK). Cytokine release was measured by incubating 1.0 mg nanoparticles in 1 ml PBS at 37° C. and measuring cytokine concentration in supernatant fractions over time by ELISA.

Imaging of T Cell-NP Interactions

10 µg of DiR-encapsulating nanoparticles conjugated to CD4 or isotype antibodies was added to C57BL/6 splenocytes (1.0×106/ml) and tumbled for 15 minutes at 37° C. in 1.5 ml microcentrifuge tubes. Cells were then stained for CD4-PE and analyzed using an Amnis Imagestream instrument.

Cell Culture

All cell culture was performed at 37° C., 5.0% CO2, 100% humidity in RPMI-1640 (Life Technologies) supplemented with 10% FBS (Atlanta Biologics), Pen/Strep, L-glutamine, MEM Vitamin solution, non-essential amino acids, sodium pyruvate, and beta-mercaptoethanol (Life Technologies).

Results

PLGA nanoparticles encapsulating TGF-β and IL-2 were visualized using scanning electron microscopy (SEM). Nanoparticles are spherical in morphology and range in size from less than 100 nm to 300 nm. Quantitative size analysis was performed using the NANOSIGHT® particle tracking system, which confirmed the size distribution and revealed a mean particle size of 168 nm (FIG. 1A).

Figure 1B:
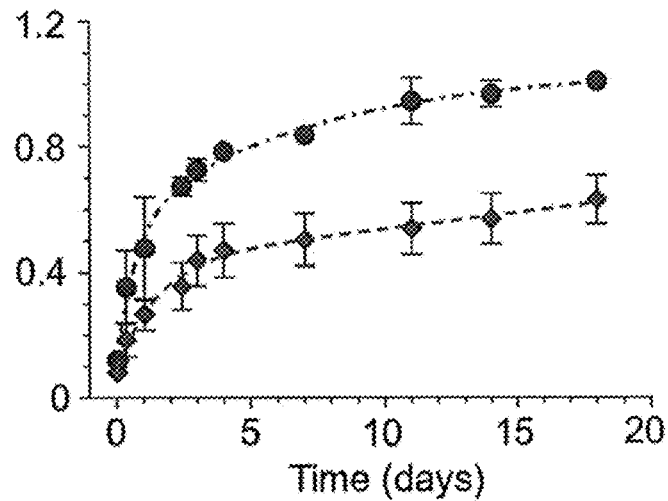
FIG. 1B is a line graph showing release kinetics of TGF-β (circles) and IL-2 (diamonds), measured by ELISA.

To measure the release kinetics of encapsulated cytokines over the course of nanoparticle degradation, the particles were incubated in PBS and ELISAs were performed on their supernatants over time. The resulting plot indicates a burst release of TGF-β and IL-2 over the first 4 days, followed by linear release for the next 14 days (FIG. 1B). At day 5 of incubation, 0.8 ng and 0.5 ng of TGF-β and IL-2, respectively, are released from each mg of nanoparticles. To verify the binding capacity of anti-CD4-conjugated nanoparticles to CD4 T cells, 1,1'-Dioctadecyl-3,3,3',3'-tetramethylindotricarbocyanine iodide, AAT Bioquest (DiR) labeled, anti-CD4-conjugated nanoparticles were incubated with mixed splenocytes. Following incubation, cells were stained for CD4-PE and analyzed using Amnis ImageStream Cytometry to visualize the particles' CD4 specificity and cellular localization. Targeting with anti-CD4 increases specific binding from 10.8% to 61.6%, while the percentage of CD4+ cells tagged with nanoparticles is enhanced from 3.97% to 73.9%. Nanoparticles bind to the outer membrane of CD4 T cells. In all subsequent experiments, nanoparticles are coated with anti-CD4 unless otherwise stated.

Example 2: Nano-Encapsulated Cytokines Generate Foxp3+ CD4 Tregs

Materials and Methods

Functional Characterization of Nano-Encapsulated IL-2

CRL-1841 cells (ATCC, Manassas, Va.) were seeded at 5.0×104 cells per well of a 96-well plate and dosed with free IL-2 or IL-2 encapsulated in untargeted nanoparticles. Fold proliferation was quantified by Coulter Counter after 4 days of culture.

Animals

C57BL/6 and BALB/c mice were purchased from Jackson Labs and Harlan, respectively, for use at 6-12 weeks of age. Mice expressing GFP as a reporter of Foxp3 expression (GFP-Foxp3 reporter mice) were generated on a C57BL/6 background as previously described (Bettelli, et al., *Nature*, 441(7090):235-8 (2006). All animal work was performed under protocols approved by the Yale Institute of Animal Care and Use Committee.

In-Vitro Treg Expansion

Freshly isolated mouse splenocytes were plated in 96-well round bottom plates at 1.0×105 cells in 0.2 ml per well. Wells were pre-coated with anti-CD3 (eBiosciences) at 2.0 ug/ml and media was supplemented with 2.0 ug/ml anti-CD28 (eBiosciences). For Treg induction conditions, media was supplemented with TGF-β and IL-2 at 5.0 ng/ml and 10 ug/ml, respectively, unless otherwise stated. For kinetic analysis of Foxp3 expression, cells were removed from culture at day 3, washed twice in media to remove unbound nanoparticles and free cytokine, and re-seeded in fresh wells containing CD3 and CD28. For Foxp3 destabilizing conditions, TGF-β and IL-6 were added at re-seeding at 5.0 and 10 ng/ml, respectively. Nanoparticles were prepared as described above and added to cells at 100 ug/ml, unless otherwise stated.

Results

Figure 2A:
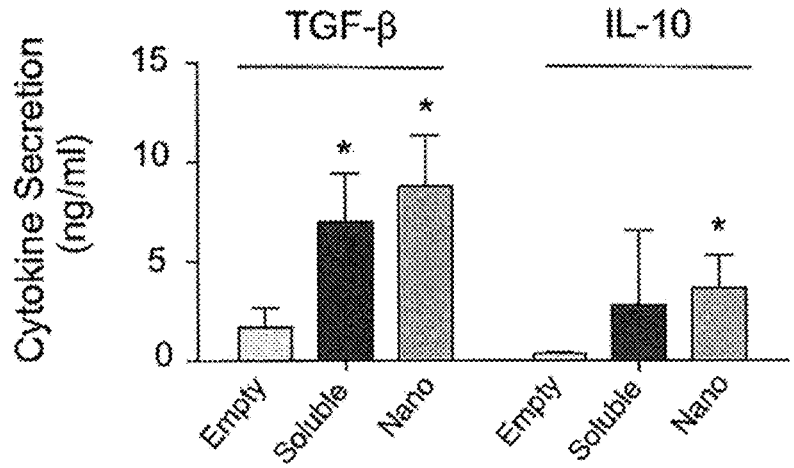
FIG. 2A is a bar graph showing TGF-β and IL-10 concentrations in the supernatant were measure by ELISA of mixed splenocytes cultured with TGF-β and IL-2 in soluble (5 ng/ml and 10 U/ml, respectively) or nano-encapsulated form (0.1 mg nanoparticle/ml) to induce CD25+Foxp3+ Tregs.
Figure 2B:
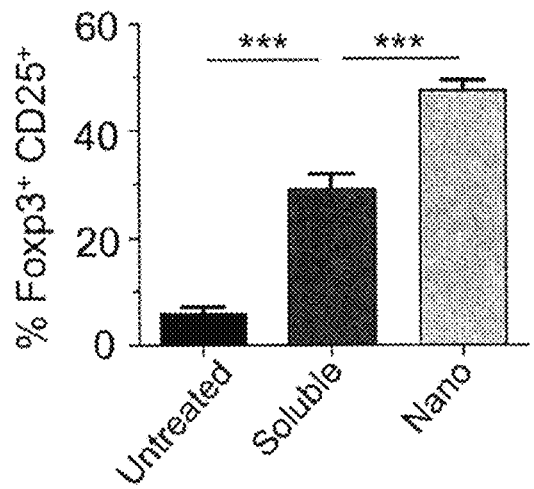
FIG. 2B is a bar graph showing % Foxp3+ CD25+ of untreated lymphocytes or lymphocytes treated with soluble or nanoparticle ("nano") encapsulated TGF-β and IL-2 (Results from 4 independent experiments are plotted (***P<0.001)).
Figure 2C:
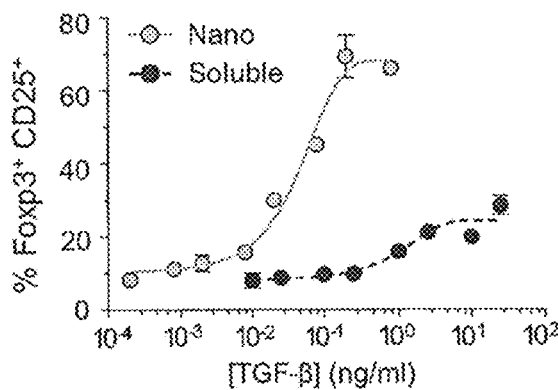
FIG. 2C is a dose-response curve showing dose responses of nano-encapsulated (solid line) and soluble (hatched line) cytokine. Values are percentages of CD4+ lymphocytes.
Figure 2D:
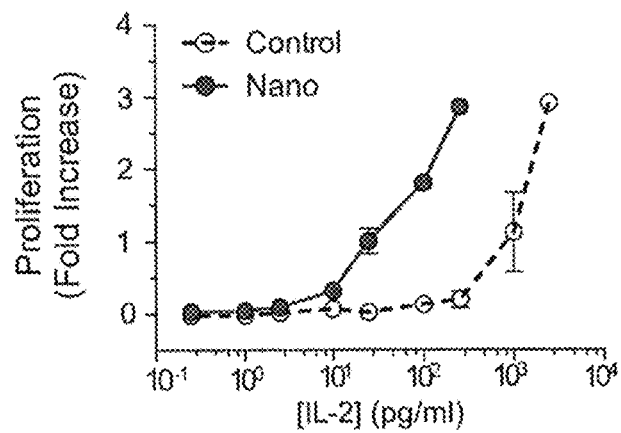
FIG. 2D is a dose-response curve showing proliferation of IL-2 dependent CTRL-1842 cells dosed with nano-encapsulated (nano, solid line) or free (control, hatched line) IL-2 and quantified after 4 days by Coulter Counter.

Foxp3-GFP reporter mouse splenocytes were depleted of CD4+CD25+Foxp3+ cells by FACS. Cells were stimulated with anti-CD3 and anti-CD28 in the presence of TGF-β and IL-2 for three days. Foxp3+CD4+ cells are generated in both the nTreg depleted and non-depleted groups (18.9% and 21.9% of lymphocytes, respectively), indicating that TGF-β and IL-2 induce Foxp3 expression from naïve CD4 cells. After 5 days of Treg induction by either nano-encapsulated or free TGF-β and IL-2, cells secreted TGF-β and IL-10 as measured by ELISA (FIG. 2A). Representative FACS plots show that Foxp3 expression is increased by nearly 2-fold using nano-encapsulated IL-2 and TGF-β compared to soluble cytokines. Cumulative data from four independent experiments shows significant differences between each group (FIG. 2B). Dose response curves show that lower concentrations of TGF-β released from 0.1 mg/ml targeted or untargeted nanoparticles is needed for Foxp3 expression compared to soluble TGF-β (FIG. 2C). IL-2 dependent cells require 10 fold less IL-2 released from nanoparticles in comparison with soluble IL-2 for equivalent proliferation (FIG. 2D).

Example 3: Functional Properties of Nanoparticle-Induced Tregs

Staining, FACS, and Cytokine Secretion Analysis

Cells were stained with CellTrace Violet (Life Technologies) following the manufacturers suggested protocol. After red blood cell lysis, splenocyte pellets were resuspended in 10 uM solution of CellTrace Violet in DPBS and incubated for 15 minutes at 37° C. The reaction was then quenched using 5× volume of RPMI+10% FBS, and cells were pelleted once more to wash away free CellTrace Violet dye. For the Treg suppressor assay (FIG. 4A-4E), responder cells were labeled with CellTrace Violet after FACS purification and plated immediately.

Fluorescent antibodies were purchased from eBiosciences and used in dilutions of 1:200 or 1:400 in FACS buffer (PBS containing 2% FBS) for surface staining. CD4 was detected using clone RM 4-4 to avoid competitive binding with nanoparticle-conjugated RM 4-5. Cells were incubated with antibodies for 20-30 minutes and washed once in FACS buffer. For experiments requiring Foxp3 staining, samples were treated with 250 ul of Fix/Perm buffer (Intracellular Fixation and Permeabilization Kit, eBiosciences) after washing off surface antibodies. After 30-60 minutes, samples were washed with 2.0 mls Penn buffer and incubated with Foxp3 antibody (clone FJK-16s, eBioscience) for 30-60 minutes. Cells were then washed with 2.0 mls Penn buffer. After staining, cells were suspended in 1% PFA until FACS analysis up to 24 hours later. All incubations in the immunostaining procedures were carried out in the dark on ice. FACS analysis was performed on either a FACScan or LSR-II (Becton Dickinson), and sorting was done on a FACSAria (Becton Dickinson). All FACS data were analyzed using FlowJo software (Tree Star Inc., Ashland, Oreg.).

TGF-β and IL-10 secretion was quantified by ELISA using kits purchased from Becton Dickinson, following the manufacturer's suggested instructions. Total TGF-β was measured by activating latent cytokine by incubating supernatants with 0.04 N HCl for 1 hour and neutralizing with NaCl. TGF-β supplied by the treatment was subtracted from the measured values to quantify secretion.

Treg Suppression Assay

Tregs were generated from Foxp3-GFP reporter mouse (Thy1.1−) splenocytes using either soluble TGF-β and IL-2 or nano-encapsulated TGF-β and IL-2 for a 5 day induction period beginning with 1×105 cells per well in 96-well U-bottom plates. At the end of culture, the percentage of CD4+Foxp3+ Tregs in each group was quantified by FACS. Cells were washed of excess nanoparticles or cytokines by centrifugation. These cells, defined collectively as the suppressor population, were mixed with FACS-purified, CellTrace Violet labeled Thy1.1+CD4+CD25− splenocytes, (defined as responder cells) at titrated frequencies and stimulated with CD3/CD28 beads (Dynabeads, Life Technologies) at a 1:2 bead-to-cell ratio for 4 days in 96-well flat-bottom plates. Samples were surface stained for CD4 and Thy1.1 and run on FACS immediately.

Proliferative Index was calculated by dividing the total number of responder cells at the end of culture by the number of parent responder cells. Total number of cells was calculated by gating on each generation and accounting for number of divisions, using an area under the curve summation formula previously reported (Roederer, et al., *Cytometry Part A: the journal of the International Society for Analytical Cytology*, 79(2):95-101. PubMed PMID: 21265003) and defined in Table 2. Initial Treg frequency, or the percentage of Thy1.1-Foxp3+ Tregs in culture at the start of the suppression phase is defined in Table 2.

Results

Figures 3A, 3B:
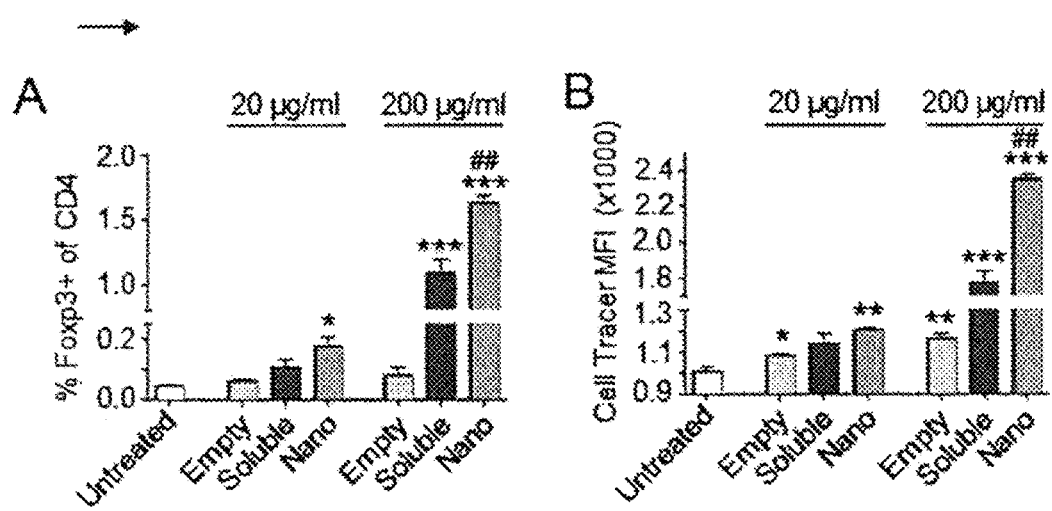
FIG. 3A is a bar graph showing Foxp3 induction after CD4+GFP-cells were sorted, stained with CellTrace Violet, and stimulated with CD3/CD28 beads for 4 days in the presence of load or empty NPs or free cytokine controls at dosages of 20 ug/ml and 200 ug/ml NP doses.
FIG. 3B is a Cell Trace Violet mean intensity is plotted (*p<0.05, p<0.01, *p<0.001 from untreated control. ##p<0.01 from soluble control) of the experiment described in FIG. 3B.

To test the effect of nanoparticle treatment on TCR-mediated cell activation, naïve CD4 cells were stimulated using CD3/CD28 coated polystyrene beads. Even under these strong effector T cell stimulatory conditions, where Treg induction is mitigated, nanoparticle treatment significantly enhanced Foxp3 expression (FIG. 3A) and inhibited effector cell proliferation (FIG. 3B), compared to soluble cytokine controls. CD4-targeted empty nanoparticles had minimal effects.

To test suppressive function, induced Tregs were washed and cultured under CD3/CD28 stimulation with responder Thy1.1+ CD4 cells at various relative fractions over a four-day period referred to as the suppression phase. For clarity, each cell population is referred to using a superscript/subscript notation defined in Table 1. Characterization terms are defined in Table 2.

TABLE 1

Superscript/subscript notation

| Notation $A_y^x$ where: | A is either the frequency f in terms of percentage, or number N of cells per sample well<br>x is the parent population from which A is gated<br>y describes the given population<br>For Example:<br>$N_{1.1+}^{CD4}$ = Number of Cells (N) per sample from a Thy1.1+ cell population that are CD4+.<br>or;<br>$f_{1.1+}^{CD4}$ = Percent frequency (f) per sample from a Thy1.1+ cell population that are CD4+. |
|---|---|

| Notation | Definition |
|---|---|
| $N_{1.1+}^{CD4}$ | Final number (per well) of responder cells (Thy1.1+) |
| $N_{1.1+,i}^{CD4}$ | Initial number (per well) of responder cells (Thy1.1+) |
| $N_{1.1-}^{CD4}$ | Final number (per well) of suppressor cells (Thy1.1+) |
| $f_{1.1+}^{CD4}$ | Final frequency (%) of responder cells (Thy1.1+) from all CD4 |
| $f_{1.1+,i}^{CD4}$ | Initial frequency (%) of responder cells (Thy1.1+) from all CD4 |
| $f_{1.1-}^{CD4}$ | Final frequency (%) of suppressor cells (Thy1.1-) from all CD4 |
| $f_{1.1-Foxp3+,i}^{CD4}$ | Initial frequency (%) of Foxp3+ suppressor cells (Thy1.1-) from all CD4 |
| $f_{Foxp3+}^{1.1-}$ | Final frequency (%) of Foxp3+ cells from suppressor (Thy1.1-) population |
| $N_{Foxp3+}^{1.1-}$ | Final number (per well) of Foxp3+ cells from suppressor (Thy1.1-) population |
| $N_{Foxp3+,i}^{1.1-}$ | Initial number (per well) of Foxp3+ cells from suppressor (Thy1.1-) population |

TABLE 2

Characterization of terms

| Term | Definition |
|---|---|
| Proliferative index, PI | $= \sum_0^g f_g^{1.1+} / \sum_0^g (f_g^{1.1+}/2^g)^a$ |
| Initial Treg fraction[b] | $= f_{1.1-Foxp3+,i}^{CD4} / (f_{1.1-foxp3+,i}^{CD4} + f_{1.1+,i}^{CD4})$ |
| Final Treg number (per well), $N_{Foxp3+}^{1.1-}$ | $= (PI) \times (f_{1.1-}^{CD4}/100) \times (f_{Foxp3+}^{1.1-}/100)^c \times 10^5$ |

Figure 4A:
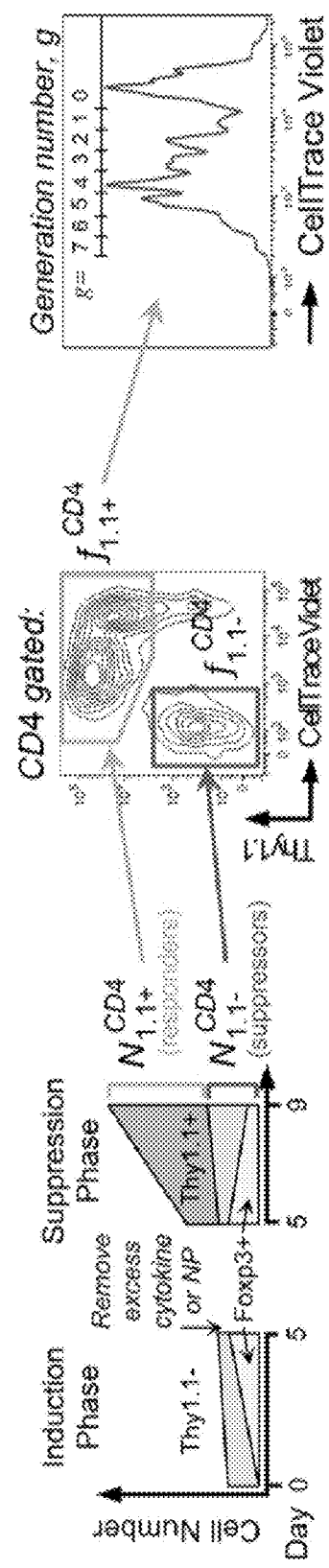
FIG. 4A is a schematic of the experimental setup shows representative cell numbers over time. The left-hand panel shows suppressor cells (Thy1.1−) were generated by either free IL-2 and TGF-β (10 U/ml and 5 ng/ml, respectively), or nanoparticles (0.1 mg/ml) for 5 days (induction phase). Foxp3+ Tregs were quantified by FACS, washed, and added in various relative Treg fractions to CD4+Thy1.1+CD25− splenocytes (responder cells). These cultures were stimulated with anti-CD3/CD28 beads in 96-well flat-bottom plates at a 1:2 bead-to-cell ratio for an additional 4 days (suppression phase). During this period, responder cells proliferated while Foxp3 expression on suppressor cells decreased. The center panel shows that following the suppression phase, suppressor and responder cells were identified by surface expression of Thy1.1 and incorporation of CellTrace Violet as shown in the representative FACS plot. The right hand panel shows that each generation of proliferated responder cells was gated as shown in the representative histogram, and gated frequencies were used to calculate proliferative index, PI, as described in Table 2.
Figures 4B, 4C, 4D, 4E:
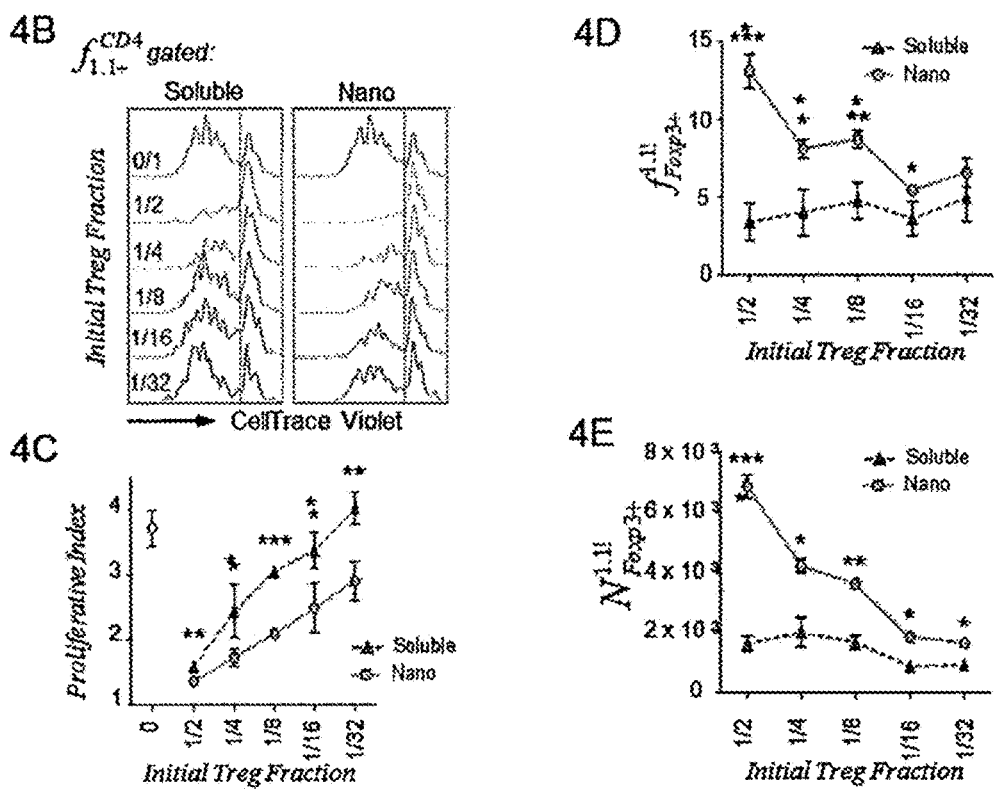
FIG. 4B is a representative CellTrace Violet dilutions across titrated initial Treg fractions shows that suppressor cells treated with nanoparticles preferentially suppressed responder proliferation.
FIG. 4C is a line graph showing the proliferative index of responder cells co-cultured with suppressor cells generated with soluble cytokines (triangles) vs. nano-encapsulated cytokines (circles) (*p<0.05, p<0.005, *p<0.001).
FIG. 4D is a line graph showing Foxp3 expression of suppressor cells plotted as a function of initial Treg fraction.
FIG. 4E is a line graph showing total numbers of remaining Foxp3+ suppressor cell numbers plotted as a function of initial Treg fraction. (*p<0.05, p<0.005, *p<0.001).

[a]Where g is generation number (0 is undivided population) and $f_g$ is frequency of events in generation g.
[b]"Initial" refers to the start of the suppression phase (day 5).
[c]$N_{Foxp3+,i}^{1.1-} + N_{1.1+,i}^{CD4} = 10^5$ A schematic of the experimental procedure as a representative cell response over time is shown (FIG. 4A (left)). At the end of the suppression phase, the resulting CD4 pool was characterized by plotting Thy1.1 expression vs. CellTrace Violet incorporation as shown in a representative FACS plot (FIG. 4A (center)). Suppressor cells were identified by absence of CellTrace Violet and Thy1.1 expression, and Responder cells were identified as Thy1.1+ CellTrace Violet intermediate-to-high, representing proliferated and undivided cells, respectively. Responder cells were plotted on a histogram according to CellTrace Violet incorporation and gated for generation number as shown in a representative histogram (FIG. 4A (right)). Representative histograms from each initial Treg fraction from each group show reduced CellTrace Violet dilutions in nanoparticle-treated groups (FIG. 4B). Proliferative Indices calculated from the above data are graphed, revealing significantly lower responder cell proliferation in nanoparticle groups at all initial Treg fractions tested (FIG. 4C). Nanoparticle-treated suppressor cells also retained Foxp3 expression to a greater extent to those induced using soluble cytokines. Foxp3 quantifications are plotted over initial Treg fraction, showing that greatest relative Foxp3 expression is found at ½ initial Treg fractions, approximately 3-fold higher than soluble controls (FIG. 4D). Absolute number of Foxp3+Tregs within the suppressor population is calculated as described in Table 2 and plotted separately (FIG. 4E). The trend is retained, in which higher initial Treg fraction correlates with Foxp3 expression in the nanoparticle groups more closely than in soluble groups.

Example 4: Foxp3 Stability of Nanoparticle-Induced Tregs

In-vitro kinetics assays were performed to test the phenotype stability of nanoparticle-induced Tregs. Mixed splenocyte cultures were incubated with free or CD4-targeted nano-encapsulated cytokine before replacement with fresh media after 3 days. As a positive control, free cytokines were replenished at day 3. By day 9 of culture, Foxp3 expression by soluble cytokine-induced cells was nearly completely lost (98% less than day 5), while Foxp3 expressing nanoparticle-induced Tregs diminished by only 34% from day 5 (FIG. 5). To evaluate Foxp3 stability under inflammatory insult, the Th17-polarizing cytokine combination TGF-β/IL-6 was added to the cultures after a 5-day Treg induction phase. At day 7, the number of CD25+Foxp3+ CD4 cells was largely retained in the nanoparticle-induced cells.

Example 5: Expansion of Tregs In-Vivo

Materials and Methods
In-Vivo Biodistribution and Treg Quantification
6-8 week old female C57/B16 mice received coumarin-6 loaded nanoparticles via intraperitoneal injection on day 0. On day 5, mice were sacrificed and secondary lymphoid tissues were collected, including the spleen, axial lymph nodes (aLN), mesenteric lymph nodes (mLN), and inguinal lymph nodes (iLN). For analysis of coumarin-6 loaded nanoparticle biodistribution, whole spleen or lymph samples were homogenized and subjected to 3 freeze/thaw cycles prior to lyophilization. Coumarin 6 was extracted by incubation of homogenized tissues in DMSO and quantified using standards generated in tissues from untreated mice, by fluorescence with excitation/emission at 460/540 nm.

For Treg quantification, tissues were processed and stained for CD4, CD25, and Foxp3 as previously described and analyzed by FACS. Cells were counted using a Coulter Counter.
Results
Next the effects of nanoparticle-mediated cytokine delivery were investigated in vivo. The biodistribution of CD4-targeted nanoparticles was investigated using coumarin 6 (C6)-loaded nanoparticles. Mice received a dose of 2.0 mgs of nanoparticles administered via intraperitoneal injection. After 5 days, animals were sacrificed and secondary lymphoid organs were collected for analysis. Extraction of C6 from the tissues showed the highest accumulation in the spleen and draining (mesenteric) lymph nodes (FIG. 6A). To assess the ability of nanoparticles to expand Tregs in-vivo, mice were injected with 2.0 mg CD4-targeted nanoparticles. After 5 days, lymph nodes were collected and Treg induction was assessed by FACS. In comparison to naïve animals (left hand bars), nanoparticle-treated animals (right hand bars) had a significantly higher frequency of Tregs in the mesenteric lymph node and spleen as measured by their frequency within the CD4 T cell compartment (FIG. 6B) (n=5 mice, *p<0.05). Total numbers of activated T cells and Tregs were not significantly enhanced (FIG. 6C).

Modifications and variations of the compositions and methods of manufacture and use thereof will be obvious to those skilled in the art from the foregoing detailed description and are intended to come within the scope of the appended claims. All references are specifically incorporated.

I claim:

1. A method of increasing donor specific Treg comprising treating isolated cells ex vivo with a composition comprising CD4-targeted nanoparticles loaded with a combination of TGF-β and IL-2.

* * * * *

UNITED STATES PATENT AND TRADEMARK OFFICE
CERTIFICATE OF CORRECTION

| | |
|---|---|
| PATENT NO. | : 10,500,157 B2 |
| APPLICATION NO. | : 16/019704 |
| DATED | : December 10, 2019 |
| INVENTOR(S) | : Tarek M. Fahmy |

It is certified that error appears in the above-identified patent and that said Letters Patent is hereby corrected as shown below:

In the Specification

In Column 1, Lines 26-28 should read as follows:
--This invention was made with government support under EB008260, HL055397, and HL085416 awarded by the National Institutes of Health, and 0609326 awarded by the National Science Foundation. The government has certain rights in the invention.--

Signed and Sealed this
Seventh Day of November, 2023

Katherine Kelly Vidal
*Director of the United States Patent and Trademark Office*